(12) United States Patent
Bombardelli et al.

(10) Patent No.: US 6,608,089 B2
(45) Date of Patent: Aug. 19, 2003

(54) DERIVATIVES OF FLAVONES, XANTHONES AND COUMARINS

(75) Inventors: Ezio Bombardelli, Milan (IT); Piero Valenti, Bologna (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/075,628

(22) Filed: Feb. 15, 2002

(65) Prior Publication Data

US 2002/0183318 A1 Dec. 5, 2002

Related U.S. Application Data

(63) Continuation of application No. PCT/EP00/08365, filed on Aug. 28, 2000.

(30) Foreign Application Priority Data

Sep. 3, 1999 (EP) ............................................. 9920912

(51) Int. Cl.$^7$ ...................... A61K 31/445; A61K 31/35; A61K 31/40; A61K 31/497; A61K 31/535

(52) U.S. Cl. ............... 514/320; 514/233.5; 514/254.11; 514/422; 514/455; 514/456; 549/388; 549/401; 548/525; 546/206; 544/151; 544/376

(58) Field of Search .................................. 514/455, 456, 514/254.11, 320, 233.5, 422; 549/388, 401; 548/525; 546/206; 544/151, 376

(56) References Cited

U.S. PATENT DOCUMENTS

| | | | |
|---|---|---|---|
| 3,513,198 A | 5/1970 | O'Brien et al. | 260/570.5 |
| 4,151,291 A | 4/1979 | Vallet | 424/281 |
| 5,023,341 A | 6/1991 | Chandraratna | 549/23 |
| 5,399,561 A | 3/1995 | Chandraratna | 514/252 |

OTHER PUBLICATIONS

Juliano, R.L. et al., "A Surface Glycoprotein Modulating Drug Permeability in Chinese Hamster Ovary Cell Mutants," Biochimica et Biophysica Acta, 455, pp. 152–162, 1976.

Higgins, C.F. et al., "A family related ATP–binding subunits coupled to many distinct biological processes in bacteria," Nature 323, pp. 448–450, 1986.

Ford, J.M. et al., "Pharmacology of Drugs That Alter Multidrug Resistance in Cancer," Pharmacological Review 42:3, pp. 155–199, 1990.

Tsuruo T. et al., "Overcoming of Vincristine Resistance in P388 Leukemia in Vivo and in Vitro through Enhanced Cytotoxicity of Vincristine and Vinblastine by Verapamil," Cancer Research 41, pp. 1967–1972, 1981.

Chauffert, B. et al., "Amiodarone–Induced Enhancement of Doxorubicin and 4'–Deoxydoxorubicin Cytotoxity to Rat Colon Cancer Cells in Vitro and In Vivo," Cancer Research 46, 825–830, 1986.

Proceedings of the American Association for Cancer Research, 34, pp. 321, 1993.

Tsuruo, T. et al., "Potentiation of Vincristine and Adriamycin Effects in Human Hemopoietic Tumor Cell Lines by Calcium Antagonists and Calmodulin Inhibitors," Cancer Research 43, pp. 2267–2272, 1983.

Ford, J.M. et al., "Structural Features Determining Activity of Phenothiazines and Related Drugs for Inhibition of Cell Growth and Reversal of Multidrug Resistance," Molecular Pharmacology, 35, pp. 105–115, 1989.

Raderer, M. et al., "Clinical Trials of Agents that Reverse Multidrug Resistance," Cancer, 72:12, pp. 3553–3563, 1993.

Petrow V. et al., "Analgesics. Part II. Some Aryloxyalkyl Oxaalkylamines," Pharm and Pharmacol. 10, pp. 86–95, 1958.

Skehan, P. et al., "New Colorimetric Cytotoxicity Assay for Anticancer–Drug Screening," J. Nat. Cancer Institute 82:13, pp. 1107–1112, 1990.

Primary Examiner—Amelia A. Owens
(74) Attorney, Agent, or Firm—Pennie & Edmonds LLP

(57) ABSTRACT

Compounds having the formula (I)

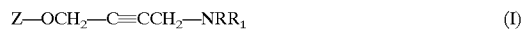

or a pharmaceutically acceptable salt or solvate thereof wherein Z can represent the formula (1A) or (1B).

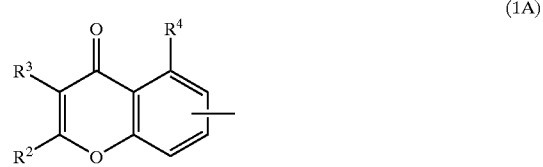

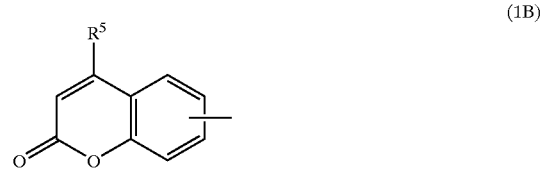

The compounds possess antiproliferative activity and are useful as modulators of multiple drug resistance in cancer chemotherapy. The compounds may also be useful for the manufacture of a medicament for the treatment or prevention of neoplasms, menopausal disorders and osteoporosis.

48 Claims, No Drawings

DERIVATIVES OF FLAVONES, XANTHONES AND COUMARINS

This application is a continuation of PCT/EP00/08365 filed Aug. 28, 2000.

FIELD OF THE INVENTION

The invention relates to a class of compounds which have a structure related to naturally and synthetically occurring flavanoids and to pharmaceutical uses of the compounds.

TECHNICAL FIELD

The development of multiple drug resistance represents an increasing problem in cancer treatment. Within the past decade several mechanisms of drug resistance of tumor cells have been identified. One type of multiple resistance (MDR) has been shown to be mediated by an energy dependent, membrane-bound efflux pump termed P-glycoprotein (PGP) (Biochem. Biophys. Acta, 455, 152, 1976). PGP represents a member of the ATP-binding cassette with low substrate specificity (Nature, 323, 448, 1986). A broad range of cytostatic drugs such as anthracyclines, epipodyphyllotoxins, actinomycin D, vinca alkaloids, colchicines and taxol are eliminated via PGP-mediate efflux. Within the past few years a variety of substances have been shown to inhibit PGP-mediated drug efflux and thereby re-establish sensitivity toward chemotherapeutic agents (Pharmacol, Rev. 42, 155, 1990). These include ion channel blockers such as verapamil (Cancer Res. 41, 1967, 1981), amiodarone (Cancer Res 46, 825, 1986), propafenone (Proc. Am. Assoc. Cancer Res. 34, 321, 1993), dihydropyridines (Cancer Res. 43, 2267, 1983) phenothiazines (Mol. Pharmacol. 35, 105, 1989). Preliminary results obtained in clinical studies clearly demonstrate that modulation of MDR might be a successful approach in haematological malignancies, but serious side effects (cardiac effects, immuno-suppression and nephrotoxicity) often preclude optimal dosage of modulators (Cancer 72, 3553, 1993). Therefore, specifically designed highly active modulators with limited side effects are urgently required.

The present invention relates to a novel class of compounds which have structures related to certain naturally occurring and synthetic flavonoids and to pharmaceutical uses thereof.

SUMMARY OF THE INVENTION

Thus according to one aspect of the present invention, there is provided a compound of Formula (I):

$$Z-OCH_2-C\equiv CCH_2-NRR^1 \qquad (I)$$

or a pharmaceutically acceptable salt or solvate thereof wherein:

R and $R^1$ are the same or different and each represents lower $C_{1-6}$ alkyl, or a carbocyclic group containing from 5 to 10 ring atoms, said ring atoms forming one or two rings wherein the or each ring contains 5 or 6 ring atoms, or R and $R^1$ taken together with the nitrogen atom to which they are attached, form a four- to eight-membered heterocyclic ring which may contain one or more additional heteroatoms selected from N, O or S, said heterocyclic ring being optionally substituted with a lower $C_{1-4}$ alkyl group or a benzyl group;

Z represents:

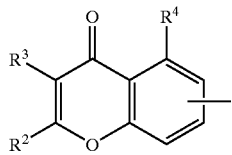

(A)

wherein
$R^2$ and $R^3$ are each independently selected from:
(i) hydrogen, (ii) a substituted or unsubstituted, preferably aromatic, carbocydic or heterocyclic group containing from 5 to 10 ring atoms, said ring atoms forming one or two rings wherein the or each ring contains 5 or 6 ring atoms, any heteroatoms being selected from N, O and S, any substituents being independently selected from the group consisting of
(a) Cl, (b) Br, (c) F, (d) OH, (e) $NO_2$, (f) $CF_3$, (g) $C_{1-4}$ lower alkyl (in particular $CH_3$), (h) $SCH_3$, (i) $NHCOCH_3$, (j) $N(R^6)(R^8)$ wherein $R^6$ and $R^8$, are the same or different and each represents H or lower $C_{1-4}$ alkyl, (k) $OR^{10}$ wherein $R^{10}$ represents H or lower $C_{1-6}$ alkyl which may be saturated or unsaturated and being unsubstituted or substituted with the group $NRR^1$ wherein R and $R^1$ is as defined above, and (I) $OCOR^{11}$ wherein $R^{11}$ represents H or lower $C_{1-4}$ alkyl,
(iii) Cl, (iv) Br, (v) F, (vi) OH, (vii) $NO_2$, (viii) a saturated or unsaturated lower $C_{1-6}$ straight or branched hydrocarbyl group which may be unsubstituted or substituted by 1, 2 or 3 substituents selected from Cl, Br, F, OMe, $NO_2$ and $CF_3$, (ix) $NHCOCH_3$, (x) $N(R^6)(R^8)$, (xi) $SR^{10}$, (xii) $OR^{10}$, and (xiii) $OCOR^{11}$ wherein $R^6$, $R^8$, $R^{10}$ and $R^{11}$ are as defined above;

or $R_2$ and $R_3$ taken together with the carbon atoms to which they are attached form a carbocyclic or heterocyclic ring having 5 or 6 ring atoms, any heteroatom being selected from N, O or S, said carbocyclic or heterocyclic ring being saturated or unsaturated, and being unsubstituted or substituted with one or more substituents selected from Cl, Br, F, OH, $NO_2$, $CF_3$, $C_{1-4}$ lower alky, $SCH_3$, $NHCOCH_3$, $N(R^6)(R^8)$, $OR^{10}$ and $OCOR^{11}$ wherein $R^6$, $R^8$, $R^{10}$ and $R^{11}$ are as defined above; and $R^4$ represents hydrogen, or $OR^{10}$ wherein $R^{10}$ is as defined above or

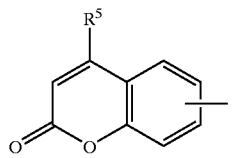

(B)

wherein $R^5$ represents hydrogen or a lower $C_{1-6}$ straight or branched hydrocarbyl group which may be unsubstituted or substituted by 1, 2 or 3 substituents selected from Cl, Br, F, OMe, $NO_2$ and $CF_3$.

DETAILED DESCRIPTION OF THE PREFERRED EMBODIMENTS

Thus in one aspect the invention provides compounds having the structure (1A'):

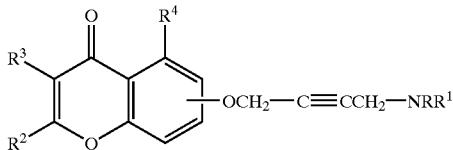

(IA')

wherein
$R^2$ and $R^3$ are each independently selected from:
(i) hydrogen, (ii) a substituted or unsubstituted, preferably aromatic, carbocyclic or heterocyclic group containing from 5 to 10 ring atoms, said ring atoms forming one or two rings, wherein the or each ring contains 5 or 6 ring atoms, any heteroatoms being selected from N, O and S, any substituents being independently selected from the group consisting of:

Cl, Br, F, OH, $NO_2$, $CF_3$, $C_{1-4}$ lower alkyl (in particular $CH_3$), $SCH_3$, $NHCOCH_3$, $N(R^6)(R^8)$, $OR^{10}$ and $OCOR^{11}$, wherein $R^6$, $R^8$, $R^{10}$ and $R^{11}$ are the same or different and each represents H or lower $C_{1-4}$ alkyl, (iii) Cl, (iv) Br, (v) F, (vi) OH, (vii) $NO_2$, (viii) a saturated or unsaturated lower $C_{1-6}$ straight or branched hydrocarbyl group which may be unsubstituted or substituted by 1, 2 or 3 substituents selected from Cl, Br, F, OMe, $NO_2$ and $CF_3$, (ix) $NHCOCH_3$, (x) $N(R^6)(R^8)$, (xi) $SR^{10}$, (xii) $OR^{10}$, and (xiii) $OCOR^{11}$ wherein $R^6$, $R^8$, $R^{10}$ and $R^{11}$ are as defined above;
or $R_2$ and $R^3$ taken together with the carbon atoms to which they are attached form a carbocyclic or heterocyclic ring having 5 or 6 ring atoms, any heteroatom being selected from N, O or S, said carbocyclic or heterocyclic ring being saturated or unsaturated, and being unsubstituted or substituted with one or more substituents selected from Cl, Br, F, OH, $NO_2$, $CF_3$, $C_{1-4}$ lower alkyl, $SCH_3$, $NHCOCH_3$, $N(R^6)(R^8)$, $OR^{10}$ and $OCOR^{11}$, wherein $R^6$, $R^8$, $R^{10}$ and $R^{11}$ are as defined above; and $R^4$ represents hydrogen, or $OR^{10}$ wherein $R^{10}$ is as defined above.

A preferred group of compounds are those wherein R, $R^1$ and $R^4$ are as defined for Formula (IA') above, and $R^2$ and $R^3$ are each independently selected from:
(i) hydrogen, (ii) a substituted or unsubstituted, preferably aromatic, carbocyclic or heterocyclic group containing from 5 to 10 ring atoms, said ring atoms forming one or two rings, wherein the or each ring contains 5 or 6 ring atoms, any heteroatoms being selected from N, O and S, any substituents being independently selected from the group consisting of:
(a) Cl, (b) Br, (c) F, (d) OH, (e) $NO_2$, (f) $CF_3$, (g) $C_{1-4}$ lower alkyl (in particular $CH_3$), (h) $SCH_3$, (i) $NHCOCH_3$, (j) $N(R^6)(R^8)$ wherein $R^6$ and $R^8$, are the same or different and each represents H or lower $C_{1-4}$ alkyl, (k) $OR^{10}$ wherein $R^{10}$ represents H or lower $C_{1-6}$ alkyl which may be saturated or unsaturated and being unsubstituted or substituted with the group $NRR^1$ wherein R and $R^1$ is as defined above, and (l) $OCOR^{11}$ wherein $R^{11}$ represents H or lower $C_{1-4}$ alkyl, (iii) Cl, (iv) Br, (v) F, (vi) OH, (vii) $NO_2$, (viii) a saturated or unsaturated lower $C_{1-6}$ straight or branched hydrocarbyl group which may be unsubstituted or substituted by 1, 2 or 3 substituents selected from Cl, Br, F, OMe, $NO_2$ and $CF_3$, (ix) $NHCOCH_3$, (x) $N(R^6)(R^8)$, (xi) $SR^{10}$, (xii) $OR^{10}$, and (xiii) $OCOR^{11}$ wherein $R^6$, $R^8$, $R^{10}$ and $R^{11}$ are as defined for Formula (I).

Within this group, $R^2$ and $R^3$ can both represent hydrogen. A further preferred group of compounds are those wherein one of $R^1$ or $R^2$ is hydrogen, and the other is selected from the group consisting of: (i) a substituted or unsubstituted, preferably aromatic, carbocyclic or heterocyclic group containing from 5 to 10 ring atoms, said ring atoms forming one or two rings, wherein the or each ring contains 5 or 6 ring atoms, any heteroatoms being selected from N, O and S, any substituents being independently selected from the group consisting of:

Cl, Br, F, OH, $NO_2$, $CF_3$, $C_{1-4}$ lower alkyl (in particular $CH_3$), $SCH_3$, $NHCOCH_3$, $N(R^6)(R^8)$, $OR^{10}$ and $OCOR^{11}$, wherein $R^6$, $R^8$, $R^{10}$ and $R^{11}$ are the same or different and each represents H or lower $C_{1-4}$ alkyl, (ii) Cl, (iii) Br, (iv) F, (v) OH, (vi) $NO_2$, (vii) a saturated or unsaturated lower $C_{1-6}$ straight or branched hydrocarbyl group which may be unsubstituted or substituted by 1, 2 or 3 substituents selected from Cl, Br, F, OMe, $NO_2$ and $CF_3$, (viii) $NHCOCH_3$, (ix) $N(R^6)(R^8)$, (x) $SR^{10}$, (xi) $OR^{10}$, and (xii) $OCOR^{11}$ wherein $R^6$, $R^8$, $R^{10}$ and $R^{11}$ are as defined for Formula (I).

Within this preferred group of compounds, a further preferred group of compounds are those wherein $R^2$ hydrogen and $R^3$ is selected from the group consisting of: (i) a substituted or unsubstituted, preferably aromatic, carbocyclic or heterocyclic group containing from 5 to 10 ring atoms, said ring atoms forming one or two rings, wherein the or each ring contains 5 or 6 ring atoms, any heteroatoms being selected from N, O and S, any substituents being independently selected from the group consisting of:

Cl, Br, F, OH, $NO_2$, $CF_3$, $C_{1-4}$ lower alkyl (in particular $CH_3$), $SCH_3$, $NHCOCH_3$, $N(R^6)(R^8)$, $OR^{10}$ and $OCOR^{11}$, wherein $R^6$, $R^8$, $R^{10}$ and $R^{11}$ are the same or different and each represents H or lower $C_{1-4}$ alkyl, (ii) Cl, (iii) Br, (iv) F, (v) OH, (vi) $NO_2$, (vii) a saturated or unsaturated lower $C_{1-6}$ straight or branched hydrocarbyl group which may be unsubstituted or substituted by 1, 2 or 3 substituents selected from Cl, Br, F, OMe, $NO_2$ and $CF_3$, (viii) $NHCOCH_3$, (ix) $N(R^6)(R^8)$, (x) $SR^{10}$, (xi) $OR^{10}$, and (xii) $OCOR^{11}$ wherein $R^6$, $R^8$, $R^{10}$ and $R^{11}$ are as defined for Formula (I).

A further preferred group of compounds are those wherein $R^3$ is hydrogen and $R^2$ is selected from the group consisting of: (i) a substituted or unsubstituted, preferably aromatic, carbocyclic or heterocyclic group containing from 5 to 10 ring atoms, said ring atoms forming one or two rings, wherein the or each ring contains 5 or 6 ring atoms, any heteroatoms being selected from N, O and S, any substituents being independently selected from the group consisting of.

Cl, Br, F, OH, $NO_2$, $CF_3$, $C_{1-4}$ lower alkyl (in particular $CH_3$), $SCH_3$, $NHCOCH_3$, $N(R^6)(R^8)$, $OR^{10}$ and $OCOR^{11}$, wherein $R^6$, $R^8$, $R^{10}$ and $R^{11}$ are the same or different and each represents H or lower $C_{1-4}$ alkyl, (ii) Cl, (iii) Br, (iv) F, (v) OH, (vi) $NO_2$, (vii) a saturated or unsaturated lower $C_{1-6}$ straight or branched hydrocarbyl group which may be unsubstituted or substituted by 1, 2 or 3 substituents selected from Cl, Br, F, OMe, $NO_2$ and $CF_3$, (viii) $NHCOCH_3$, (ix) $N(R^6)(R^8)$, (x) $SR^{10}$, (xi) $OR^{10}$, and (xii) $OCOR^{11}$ wherein $R^6$, $R^8$, $R^{10}$ and $R^{11}$ are as defined for Formula (I).

A further preferred embodiment of the present invention are compounds wherein $R^2$ represents a substituted or unsubstituted, preferably aromatic, carbocyclic or heterocyclic group containing from 5 to 10 ring atoms, said ring atoms forming one or two rings, wherein the or each ring contains 5 or 6 ring atoms, any heteroatoms being selected from N, O and S, any substituents being independently selected from the group consisting of: Cl, Br, F, OH, $NO_2$, $CF_3$, $C_{1-4}$ lower alkyl (in particular $CH_3$), $SCH_3$, $NHCOCH_3$, $N(R^6)(R^8)$, $OR^{10}$ and $OCOR^{11}$, wherein $R^6$, $R^8$, $R^{10}$ and $R^{11}$ are as defined as for Formula (I). For these compounds, $R^3$ is preferably selected from the group consisting of H, Cl, Br, F, OH, $NO_2$, a saturated or unsaturated lower $C_{1-6}$ straight or branched hydrocarbyl group which may be unsubstituted or substituted by 1, 2 or 3 substituents selected from Cl, Br, F, OMe, $NO_2$ and $CF_3$,
$NHCOCH_3$, $N(R^6)(R^8)$, $SR^{10}$, $OR^{10}$, and $OCOR^{11}$ wherein $R^6$, $R^8$, $R^{10}$ and $R^{11}$ are as defined for Formula (I).

Alternatively compound $R^3$ may represent a substituted or unsubstituted, preferably aromatic, carbocyclic or heterocyclic group containing from 5 to 10 ring atoms, said ring atoms forming one or two rings, wherein the or each ring contains 5 or 6 ring atoms, any heteroatoms being selected from N, O and S, any substituents being independently selected from the group consisting of:

Cl, Br, F, OH, $NO_2$, $CF_3$, $C_{1-4}$ lower alkyl (in particular $CH_3$), $SCH_3$, $NHCOCH_3$, $N(R^6)(R^8)$, $OR^{10}$ and $OCOR^{11}$, wherein $R^6$, $R^8$, $R^{10}$ and $R^{11}$ are as defined for Formula (I).

For these compounds, $R^2$ is preferably selected from the group consisting of H, Cl, Br, F, OH, $NO_2$, a saturated or unsaturated lower $C_{1-6}$ straight or branched hydrocarbyl group which may be unsubstituted or substituted by 1, 2 or 3 substituents selected from Cl, Br, F, OMe, $NO_2$ and $CF_3$,
$NHCOCH_3$, $N(R^6)(R^8)$, $SR^{10}$, $OR^{10}$, and $OCOR^{11}$ wherein $R^6$, $R^8$, $R^{10}$ and $R^{11}$ are as defined for Formula (I).

Where $R^2$ and/or $R^3$ represents a substituted carbocyclic or heterocyclic group, the substituents on the carbocyclic or heterocyclic group are preferably selected from OH or $OR^{10}$ wherein $R^{10}$ is as defined for Formula (I).

A particularly preferred carbocyclic group is phenyl or phenyl substituted with 1 to 3 OH or $OR^{10}$ groups. For these compounds, $R^{10}$ preferably represents methyl or

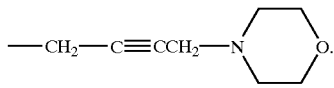

Also preferred are compounds wherein one of $R^2$ or $R^3$ represents H or a lower $C_{1-6}$ straight or branched hydrocarbyl group, with methyl being especially preferred.

The invention also provides a compound of Formula (I) having the structure (IA''):

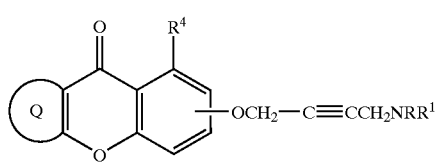

(IA'')

wherein R, $R^1$ and $R^4$ are as defined as for Formula (I), and $R^2$ and $R^3$ taken together represent Ring Q, said Ring Q being a carbocyclic or heterocyclic ring having 5 or 6 ring atoms, any heteroatom being selected from N, O or S, said carbocyclic or heterocyclic ring being saturated or unsaturated and being unsubstituted or substituted with one or more substituents selected from Cl, Br, F, OH, $NO_2$, $CF_3$; $C_{1-4}$ lower alkyl, $SCH_3$, $NHCOCH_3$, $N(R^6)(R^8)$, $OR^{10}$ and $OCOR^{11}$, wherein $R^6$, $R^8$, $R^{10}$ and $R^{11}$ are as defined as for Formula (I).

For these compounds Ring Q preferably represents a carbocyclic or heterocyclic aromatic ring, any heteroatom being selected from N, O or S, said ring being unsubstituted or substituted with one or more substituents selected from Cl, Br, F, OH, $NO_2$, $CF_3$, $C_{1-4}$ lower alkyl, $SCH_3$, $NHCOCH_3$, $N(R^6)(R^8)$, $OR^{10}$ and $OCOR^{11}$, wherein $R^6$, $R^8$, $R^{10}$ and $R^{11}$ are as defined as in Formula (I). Particularly preferred are those compounds wherein Ring Q represents a benzene or pyridine ring.

The substituent Z may be attached to any position in the aromatic ring. Thus the compounds of Formula (IA') or (IA'') described above include compounds having the structures (IA)x, (IA)y and (IA)z:

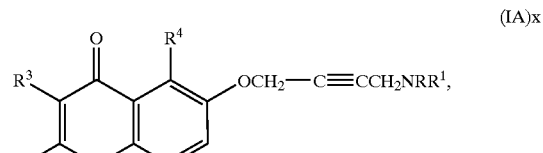

(IA)x

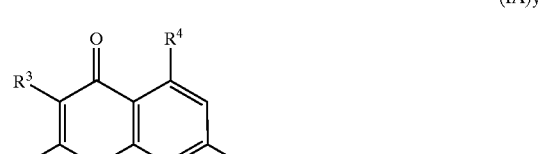

(IA)y

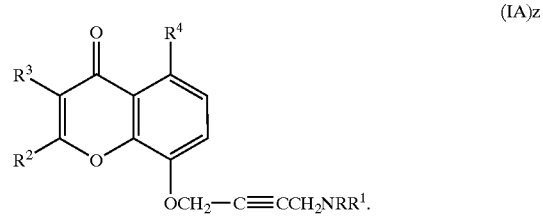

(IA)z wherein R, $R^1$, $R^2$, $R^3$ and $R^4$ are as defined above.

For the compounds of Formula (IA') or (IA'') described above, $R^4$ preferably represents H, OH or $OCH_3$.

The invention further provides compounds of Formula (I) having the structure (IB):

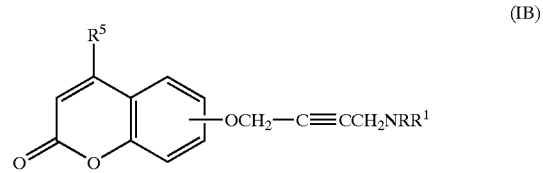

(IB)

wherein R and $R^1$ are as defined for Formula (I) and $R^5$ represents H or a lower $C_{1-6}$ straight or branched hydrocarbyl group which may be unsubstituted or substituted by 1, 2 or 3 substituents selected from Cl, Br, F, OMe, $NO_2$ and $CF_3$. In a preferred embodiment, $R^5$ represents H or methyl.

For the compounds of Formula (IB) described above, the substituent Z may be attached to any position in the aromatic ring. Thus the compounds of Formula (IB) described above include compounds having the structures (IB)w, (IB)x, (IB)y and (IB)z:

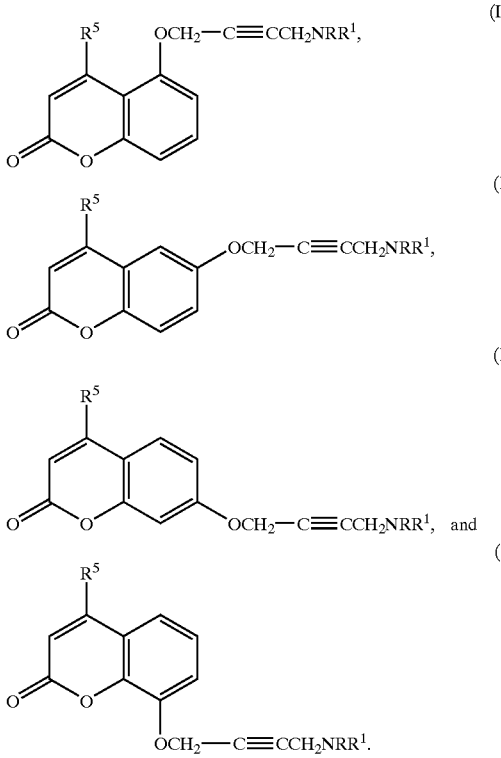

wherein R, $R^1$ and $R^5$ are as defined for Formula (I).

For the compounds of Formulae (I), (IA'), (IA") or (IB), the substituent R and $R^1$ are the same or different and preferably each represents a $C_{1-4}$ alkyl group or a $C_{5-8}$ cycloalkyl group. Within this group of compounds, R and $R^1$ are preferably independently selected from methyl, ethyl, propyl, cyclopropyl or a cyclohexyl group.

In a preferred group of compounds, the R and $R^1$ groups taken together with the nitrogen atom to which they are attached, form a four- to eight-membered heterocyclic ring. Of these, it is preferred that R and $R^1$ taken together with the nitrogen atom to which they are attached, form a pyrrolidine, piperidine, piperazine, N-methylpiperazine, N-benzylpiperazine or a morpholine group.

It will be appreciated that the compounds of Formula (I) contain a basic amino function and thus may be converted to acid addition salts, with pharmacologically acceptable acids, e.g. hydrochloric acid and phosphoric acid. Such salts are also included in the present invention.

The compounds of Formula (I) may be conveniently prepared by a process comprising the steps of:
(i) reacting a hydroxy derivative, Z—OH, with propargyl bromide to form an alkyne, Z—OCH$_2$C≡H; and
(ii) reacting the alkyne Z—OCH$_2$C≡H with an amine HNRR$^1$. Such a process forms a further aspect of the present invention.

The invention further provides a compound of Formula (I) as defined above for use as a modulator of multiple drug resistance in cancer chemotherapy or an antiproliferative medicament. In particular, the compounds of Formula (I) are especially useful for the modulation of multiple drug resistance mediated by P-glycoprotein.

The compounds of Formula (I) as defined above may also be useful for the manufacture of a medicament for the treatment or prevention of neoplasms, particularly those located in the uterus, ovary or breast. Further the compounds Formula (I) may be especially useful for the manufacture of a medicament for the treatment of paclitaxel- and docetaxel-resistant cancer cells.

The compounds of Formula (I) may also advantageously be used as an antiproliferative medicament in combination therapies involving the combined use of a compound of Formula (I) with one or more anti-neoplastic or cytostatic agents, such as paclitaxel or docetaxel. The combination therapy may involve simultaneous or successive administration of a compound of Formula (I) with one or more antineoplastic or cytostatic agents, including anthracyclines, epipodophyllotoxins, actinomycin D, vinca alkaloids, colchicines, paclitaxel or docetaxel. Such combination therapy forms a further aspect of the invention.

The compounds of the invention may also be useful in the manufacture of a medicament for the treatment or prevention of menopausal disorders and osteoporosis.

The invention further provides a pharmaceutical composition comprising one of more of the compounds of Formula (I) in combination with one or more pharmaceutically acceptable excipients. Such a composition may also comprise one or more antineoplastic or cytostatic agents, such as paclitaxel or docetaxel.

The invention will now be described by way of illustrative examples and with reference to the accompanying formulae drawings.

EXAMPLES

Example 1

General Conditions to Obtain the Propynyloxy Derivatives

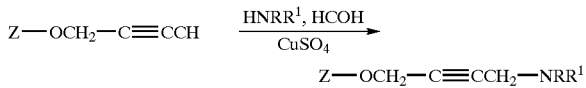

A mixture of hydroxy derivative (0.01 mol), $K_2CO_3$ (0.02 mol), KI (0.001 mol), propargyl bromide (0.015 mol) and acetone (100 mL) was refluxed 10 h and hot filtered. The solvent was evaporated and the residue was crystallized with a suitable solvent.

Example 2

Preparation of 7-propynyloxy-4-methoxyisoflavone

A mixture of 7-hydroxy-4'-methoxyisoflavone (2.68 g, 0.01 mol), $K_2CO_3$ (2.8 g, 0.02 mol), KI (0.166 g, 0.001 mol), propargyl bromide (1.78 g, 0.015 mol) and acetone (100 mL) was refluxed 10 h and hot filtered. The solvent was evaporated and the residue was crystallized by toluene. This yields 2.75 g of a product with the following characterstics: m.p.145–146° C.; $^1$H NMR (CDCl$_3$) δ: 2.6 (m, 1H), 3.83 (s, 3H), 4.8 (s, 2H), 6.93–8.27 (m, 8H).

Example 3

Preparation of 7-propynyloxyisoflavone

A mixture of 7-hydroxyisoflavone (2.38 g, 0.01 mol), $K_2CO_3$ (2.8 g, 0.02 mol), KI (0.166 g, 0.001 mol), propargyl bromide (1.78 g, 0.015 mol) and acetone (100 mL was refluxed 10 h and hot filtered. The solvent was evaporated and the residue was crystallized by toluene. This yields 2.1 g of a product with the following characteristics: m.p. 130–131° C.; $^1$H NMR (CDCl$_3$) δ: 2.6 (m, 1H), 4.8 (s, 2H), 6.99–8.28 (m, 7H).

Example 4

Preparation of 7-propynyloxy-2-methyl-4'-methoxyisoflavone

A mixture of 7-hydroxy-2-methyl-4'-methoxyisoflavone (2.82 g, 0.01 mol), K$_2$CO$_3$ (2.8 g, 0.02 mol), Kl (0.166 g, 0.001 mol), propargyl bromide (1.78 g, 0.015 mol) and acetone (100 mL) was refluxed 10 h and hot filtered. The solvent was evaporated and the residue was crystallized by toluene. This yields 2.24 g of a product with the following characteristics: m.p. 139–140° C.; $^1$H NMR (CDCl$_3$) δ: 2.29 (s, 3H), 2.6 (m, 1H), 3.85 (s, 3H), 4.75 (s, 2H), 6.93–8.17 (m, 7H).

Example 5

Preparation of 7-propynyloxy-5-hydroxy-4'-methoxyisoflavone

A mixture of 5,7-dihydroxy-4'-methoxyisoflavone (2.84 g, 0.01 mol), K$_2$CO$_3$ (2.8 g, 0.02 mol), Kl (0.166 g, 0.001 mol), propargyl bromide (1.78 g 0.015 mol) and acetone (100 mL) was refluxed 10 h and hot filtered. The solvent was evaporated and the residue was crystallized by toluene. This yields 2.25 g of a product with the following characteristics: m.p. 174–176° C.; $^1$H NMR (CDCl$_3$) δ: 2.6 (m, 1H), 3.86 (s, 3H), 4.8 (s, 2H), 647–7.91 (m, 7H), 12.90 (s, 1H).

Example 6

Preparation of 7,4'-dipropynyloxyisoflavone

A mixture of 5,7-dihydroxy-4'-methoxyisoflavone (2.54 g, 0.01 mol), K$_2$CO$_3$ (2.8 g, 0.02 mol), Kl (0.166 g, 0.001 mol), propargyl bromide (1.72 g, 0.015 mol) and acetone (100 mL) was refluxed 10 h and hot filtered. The solvent was evaporated and the residue was crystallized by toluene. This yields 2.31 g of a product with the following characteristics: m.p. 162–163° C.; $^1$H NMR (CDCl$_3$) δ: 2.44 (m, 1H, CH), 2.57 (m, 1H), 4.54 (s, 2H), 4.56 (s, 2H), 6.85–8.08 (m, 8H).

Example 7

Preparation of 1-propynyloxyxanthen-9-one

A mixture of 3-hydroxyanthen-9-one (2.12 g, 0.01 mol), K$_2$CO$_3$ (2.8 g, 0.02 mol), Kl (0.166 g, 0.001 mol), propargyl bromide (1.78 g, 0.015 mol) and acetone (100 mL) was refluxed 10 h and hot filtered. The solvent was evaporated and the residue was crystallized by toluene. This yields 2.0 g of a product with the following characteristics: m.p. 168–169° C.; $^1$H NMR (CDCl$_3$) δ: 2.56 (m, 1H), 4.94 (s, 2H), 6.95–8.33 (m, 7H).

Example 8

Preparation of 2-propynyloxyxanthen-9-one

A mixture of 2-hydroxyxanthen-9-one (2.12 g, 0.01 mol), K$_2$CO$_3$ (2.8 g, 0.02 mol), Kl (0.166 g, 0.001 mol), propargyl bromide (1.78 g, 0.015 mol) and acetone (100 mL) was refluxed 10 h and hot filtered. The solvent was evaporated and the residue was crystallized by toluene. This yields 2.25 g of a product with the following characteristics: m.p.153–154° C.; $^1$H NMR (CDCl$_3$) δ: 2.58 (m, 1H), 4.8 (s, 2H), 7.35–8.38 (m, 7H).

Example 9

Preparation of 3-propynyloxyxanthen-9-one

A mixture of 3-hydroxyxanthen-9-one (2.12 g, 0.01 mol), K$_2$CO$_3$ (2.8 g, 0.02 mol), Kl (0.166 g, 0.001 mol), propargyl bromide (1.78 g, 0.015 mol) and acetone (100 mL) was refluxed 10 h and hot filtered. The solvent was evaporated and the residue was crystallized by toluene. This yields 2.25 g of a product with the following characteristics: m.p.142–144° C.; $^1$H NMR (CDCl$_3$) δ: 2.61 (m, 1H), 4.84 (s, 2H), 6.98–8.38 (m, 7H).

Example 10

Preparation of 7-propynyloxyflavone

A mixture of 7-hydroxyflavone (2.38 g, 0.01 mol), K$_2$CO$_3$ (2.8 g, 0.02 mol), Kl (0.166 g, 0.001 mol), propargyl bromide (1.78 g, 0.015 mol) and acetone (100 mL) was refluxed 10 h and hot filtered. The solvent was evaporated and the residue was crystallized by toluene. This yields 2.58 g of a product with the following characteristics: m.p. 199–200° C.; $^1$H NMR (CDCl$_3$) δ: 2.6 (m, 1H), 4.8 (s, 2H), 6.75–8.18 (m, 9H).

Example 11

Preparation of 7-propynyloxy-3-methylflavone

A mixture of 7-hydroxy-3-methylflavone (2.52 g, 0.01 mol), K$_2$CO$_3$ (2.8 g, 0.02 mol), Kl (0.166 g, 0.001 mol), propargyl bromide (1.78 g, 0.015 mol) and acetone (100 mL) was refluxed 10 h and hot filtered. The solvent was evaporated and the residue was crystallized by toluene. This yields 2.32 g of a product with the following characteristics: m.p. 179–180° C.; $^1$H NMR (CDCl$_3$) δ: 2.15 (s, 3H), 2.69 (m, 1H), 4.8 (s, 2H), 6.95–8.25 (m, 8H).

Example 12

Preparation of 7-propynyloxy-4-methylcoumarin

A mixture of 7-hydroxy-4-methylcoumarin (1.76 g, 0.01 mol), K$_2$CO$_3$ (2.8 g, 0.02 mol), Kl (0.166 g, 0.001 mol), propargyl bromide (1.78 g, 0.015 mol) and acetone (100 mL) was refluxed 10 h and hot filtered. The solvent was evaporated and the residue was crystallized by toluene. This yields 1.93 g of a product with the following characteristics: m.p.140–141° C.; $^1$H NMR (CDCl$_3$) δ: 2.4 (s), 2.69 (m), 4.8 (s, 2H), 6.15–7.58 (m, 4H).

Example 13

General Conditions to Obtain the Aminopropynyloxy Derivatives

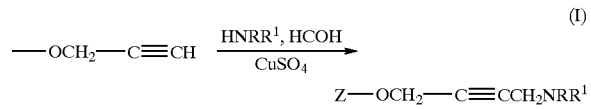

(I)

A solution of formaldehyde (0.5 ml), selected amine (6 mmol) and CuSO$_4$ (0.1 g) in EtOH/H$_2$O (20 mL) was added to a solution of propynyloxy derivative (4.6 mmol) in EtOH/H$_2$O (20 mL). H$_2$SO$_4$ was added until pH 8 and the mixture was refluxed 24 h. NH$_3$ (30 mL) was added and the mixture was extracted with ether. After evaporation of the solvent the residue was purified by flash-chromatography (eluent: toluene/acetone 4/1) and crystallized by suitable solvent

Example 14

7-(4-Piperldinobut-2-yn)-oxy-4'-methoxyisoflavone (See Accompanying Formula Drawing VIB 15)

A solution of formaldehyde (1 ml), piperidine (0.85 g, 0.01 mol) and CuSO$_4$ (0.2 g) in EtOH/H$_2$O (40 mL) was added to a solution of propynyloxy derivative (3.08 g, 0.01 mol) in EtOH/H$_2$O (40 mL). H$_2$SO$_4$ was added until pH 8 and the mixture was refluxed 24 h. NH$_3$ (60 mL) was added and the mixture was extracted with ether. After evaporation of the solvent the residue was purified by flash-chromatography (eluent: toluene/acetone 4/1) and crystallized by ligroin. This yields 1.63 g of a product with the following characteristics: m.p. 95–97° C.; $^1$H NMR δ: 1.73–1.98 (m, 2H), 1.52–1.68, (q, 4H), 2.4–2.55 (t, 4H), 3.3 (s, 2H), 3.85 (s, 3H), 4.85 (s, 2H), 6.9–8.25 (m, 8H).

Example 15

7(4-Morpholinobut-2-yn)-oxy-4'-methoxylsoflavone (See Accompanying Formula Drawing VIB 17)

A solution of formaldehyde (1 ml), morpholine (0.87 g, 0.01 mol) and CuSO$_4$ (0.2 g) in EtOH/H$_2$O (40 mL) was added to a solution of propynyloxy derivative (3.08 g, 0.01 mol) in EtOH/H$_2$O (40 mL). H$_2$SO$_4$ was added until pH 8 and the mixture was refluxed 24 h. NH$_3$ (60 mL) was added and the mixture was extracted with ether. After evaporation of the solvent the residue was purified by flash-chromatography (eluent: toluene/acetone 4/1) and crystallized by ligroin. This yields 1.62 g of a product with the following characteristics: m.p. 98–100° C.; $^1$H NMR δ: 2.43–2.61 (m, 4H), 3.3 (s, 2H), 3.6–3.78 (m, 4H), 3.78 (s, 3H), 4.75 (s, 2H), 6.9–8.3 (m, 8H).

Example 16

7-[4-(4-Benzyl-piperazin-1-yl)-but-2-yn]-oxy-4'-methoxyisoflavone (See Accompanying Formula Drawing VIB 16)

A solution of formaldehyde (1 ml), benzylpiperazine (1.76 g, 0.01 mol) and CuSO$_4$ (0.2 g) in EtOH/H$_2$O (40 ml) was added to a solution of propynyloxy derivative (3.08 g, 0.01 mol) in EtOH/H$_2$O (40 mL). H$_2$SO$_4$ was added until pH 8 and the mixture was refluxed 24 h. NH$_3$ (60 mL) was added and the mixture was extracted with ether. After evaporation of the solvent the residue was purified by flash-chromatography (eluent toluene/acetone 4/1) and crystallized by ligroin. This yields 1.1 g of a product with the following characteristics: m.p. 98–100° C.; $^1$H NMR δ: 2.45–2.65 (m, 8H), 3.35 (s, 2H), 3.52 (s, 2H), 3.85 (s, 3H), 4.85 (s, 2H), 6.95–8.27 (m, 13H).

Example 17

7--Pyrrolidinobut-2-yn)-oxy-4'-methoxyisoflavone (See Accompanying Formula Drawing VIB 91)

A solution of formaldehyde (1 ml), pyrrolidine (0.71 g, 0.01 mol) and CuSO$_4$ (0.2 g) in EtOH/H$_2$O (40 mL) was added to a solution of propynyloxy derivative (3.08 g, 0.01 mol) in EtOH/H$_2$O (40 mL). H$_2$SO$_4$ was added until pH 8 and the mixture was refluxed 24 h. NH$_3$ (60 mL) was added and the mixture was extracted with ether. After evaporation of the solvent the residue was purified by flash-chromatography (eluent: toluene/acetone 4/1) and crystallized by ligroin. This yields 0.8 g of a product with the following characteristics: m.p. 111–112° C.; $^1$H NMR δ: 1.68–1.83 (m, 4H), 2.6–2.65 (m, 4H), 3.5 (m, 2H), 3.85 (s, 3H), 4.83 (m, 2H), 6.96–8.26 (m, 8H).

Example 18

7(4-Diethylaminobut-2-yn)-oxy-4'-methoxyisoflavone (see Accompanying Formula Drawing VIB 90)

A solution of formaldehyde (1 ml), diethylamine (0.73 g, 0.01 mol) and CuSO$_4$ (0.2 g) in EtOH/H$_2$O (40 mL) was added to a solution of propynyloxy derivative (3.08 g, 0.01 mol) in EtOH/H$_2$0 (40 mL). H2SO4 was added until pH 8 and the mixture was refluxed 24 h. NH$_3$ (60 mL) was added and the mixture was extracted with ether. After evaporation of the solvent the residue was purified by flash-chromatography (eluent: toluene/acetone 4/1) and crystallized by ligroin. This yields 1.2 g of a product with the following characteristics: m.p. 73–75° C.; $^1$H NMR δ: 1 (t, 6H), 2.5 (q, 4H), 3.49 (s, 2H), 3.85 (s, 3H), 4.85 (s, 2H), 6.95–8.28 (m, 8H)

Example 19

7(44Diethylaminobut-2-yn)-oxyisoflavone (See Accompanying Formula Drawing VIB 92)

A solution of formaldehyde (1 ml), diethylamine (0.73 g, 0.01 mol) and CuSO$_4$ (0.2 g) in EtOH/H$_2$O (40 mL) was added to a solution of propynyloxy derivative (2.94 g, 0.01 mol) in EtOH/H$_2$O (40 mL). H$_2$SO$_4$ was added until pH 8 and the mixture was refluxed 24 h. NH$_3$ (60 mL) was added and the mixture was extracted with ether. After evaporation of the solvent the residue was purified by flash-chromatography (eluent: toluene/acetone 4/1) and crystallized by ligroin. This yields 0.62 g of a product with the following characteristics: m.p. 79–80° C.; $^1$H NMR δ: 1.03 (t, 6H), 2.5 (q, 4H), 3.49 (s, 2H), 4.84 (s, 2H), 7.0–8.26 (m, 9H).

Example 20

7-(4-Morpholinobut-2-yn)-oxyisoflavone (See Accompanying Formula Drawing VIB 93)

A solution of formaldehyde (1 ml), morpholine (0.87 g, 0.01 mol) and CuSO$_4$ (0.2 g) in EtOH/H$_2$O (40 mL) was added to a solution of propynyloxy derivative (2.94 g, 0.01 mol) in EtOH/H$_2$O (40 mL). H$_2$SO$_4$ was added until pH 8 and the mixture was refluxed 24 h. NH$_3$ (60 mL) was added and the mixture was extracted with ether. After evaporation of the solvent the residue was purified by flash-chromatography (eluent: toluene/acetone 4/1) and crystallized by ligroin. This yields 1.5 g of a product with the following characteristics: m.p. 104–105° C.; $^1$H NMR δ: 2.5–2.6 (m, 4H), 3.35 (s, 2H), 3.75 (m, 4H), 4.85 (m, 2H), 6,95–8.22 (m, 9H).

Example 21

7-(4-Morpholinobut-2-yn)-oxy-2-methyl-4'-methoxyisoflavone (See Accompanying Formula Drawing VIB 105)

A solution of formaldehyde (1 ml), morpholine (0.87 g, 0.01 mol) and CuSO$_4$ (0.2 g) in EtOH/H$_2$O (40 mL) was added to a solution of propynyloxy derivative (32 g, 0.01 mol) in EtOH/H$_2$O (40 mL). H$_2$SO$_4$ was added until pH 8 and the mixture was refluxed 24 h. NH$_3$ (60 mL) was added and the mixture was extracted with ether. After evaporation of the solvent the residue was purified by flash-chromatography (eluent: toluene/acetone 4/1) and crystallized by ligroin. This yields 1.2 g of a product with the following characteristics: m.p. 136–139° C.; $^1$H NMR δ: 2.15 (s, 3H), 2.5–2.6 (m, 4H), 3.35 (s, 2H), 3.7 (m, 4H), 4.7 (m, 2H), 6.95–8.25 (m, 8H).

Example 22

7-(4-Morpholinobut-2-yn)-oxy-5-hydroxy4'-methoxyisoflavone (See Accompanying Formula Drawing VIB 102)

A solution of formaldehyde (1 ml), morpholine (0.87 g, 0.01 mol) and CuSO$_4$ (0.2 g) in EtOH/H$_2$O (40 mL) was added to a solution of propynyloxy)y derivative (32 g, 0.01 mol) in EtOH/H$_2$O (40 mL). H2SO$_4$ was added until pH 8 and the mixture was refluxed 24 h. NH$_3$ (60 mL) was added and the mixture was extracted with ether. After evaporation of the solvent the residue was purified by flash-chromatography (eluent toluene/acetone 4/1) and crystallized by ligroin. This yields 0.84 g of a product with the following characteristics: oil, hydrochloric salt m.p. 120–123° C. (methanol-ether); $^1$H NMR δ: 2.3 (m, 4H), 3.3 (s, 2H), 3.7 (m, 4H), 3.85 (s, 3H), 4.85 (m, 2-H), 6.48–7.90 (m, 7H), 12.85 (s, 1H).

Example 23

7-4-Bis-Morpholinobut-2-yn)-oxyisoflavone (See Accompanying Formula Drawing VIB 97)

A solution of formaldehyde (1 ml), morpholine (0.87 g, 0.01 mol) and CuSO$_4$ (0.2 g) in EtOH/H$_2$O (40 mL) was added to a solution of propynyloxy derivative (32 g, 0.01 mol) in EtOH/H20 (40 mL). H2SO4 was added until pH 8 and the mixture was refluxed 24 h. NH$_3$ (60 mL) was added and the mixture was extracted with ether. After evaporation of the solvent the residue was purified by flash-chromatography (eluent toluene/acetone 4/1) and crystallized by ligroin. This yields 1.06 g of a product with the following characteristics: m.p. 158–159° C.; $^1$H NMR δ: 2.55 (m, 8H), 3.34 (s, 4H), 3.74 (m, 8H), 4.7 (s, 2H), 4.85 (s, 2H), 6.98–8.26(m, 8H).

Example 24

7-(4-Morpholinobut-2-yn)oxyflavone (See Accompanying Formula Drawing VIB 103)

A solution of formaldehyde (1 ml), morpholine (0.87 g, 0.01 mol) and CuSO$_4$ (0.2 g) in EtOH/H$_2$O (40 mL) was added to a solution of propynyloxy derivative (2.94 g, 0.01 mol) in EtOH/H$_2$O (40 mL). H$_2$SO$_4$ was added until pH 8 and the mixture was refluxed 24 h. NH$_3$ (60 mL) was added and the mixture was extracted with ether. After evaporation of the solvent the residue was purified by flash-chromatography (eluent: toluene/acetone 4/1) and crystallized by ligroin. This yields 0.75 g of a product with the following characterstics: m.p. 126–127° C.; $^1$H NMR δ: 2.56 (m, 4H), 3.35 (s, 2H), 3.7 (m, 4H), 4.86 (m, 2H), 6.79–8.2 (m, 9H). Mass: m/z 374 (M+, 14.38), 238 (100),137 (82.79).

Example 25

7-(4-Morpholinobut-2-yn)-oxy-3-methylflavone (See Accompanying Formula Drawing VIB 104)

A solution of formaldehyde (1 ml), morpholine (0.87 g, 0.01 mol) and CuSO$_4$ (0.2 g) in EtOH/H$_2$O (40 mL) was added to a solution of propynyloxy derivative (3.09 g, 0.01 mol) in EtOH/H$_2$O (40 mL). H$_2$SO$_4$ was added until pH 8 and the mixture was refluxed 24 h. NH$_3$ (60 mL) was added and the mixture was extracted with ether. After evaporation of the solvent the residue was purified by flash-chromatography (eluent: toluene/acetone 4/1) and crystallized by ligroin. This yields 0.78 g of a product with the following characteristics: m.p.139–140° C.; $^1$H NMR S: 2.13 (s, 3H), 2.6 (m, 4H), 3.35 (m, 2H), 3.8 (m, 4H), 4.03 (s, 2H), 6.85–8.10(m, 8H).

Example 26

7-(4-Morpholinobut-2-yn)-oxyoethylcoumarin (See Accompanying Formula Drawing VIB 95)

A solution of formaldehyde (1 ml), morpholine (0.87 g, 0.01 mol) and CuSO$_4$ (0.2 g) in EtOH/H$_2$O (40 mL) was added to a solution of propynyloxy derivative (2.14 g, 0.01 mol) in EtOH/H$_2$O (40 mL). H2SO$_4$ was added until pH 8 and the mixture was refluxed 24 h. NH$_3$ (60 mL) was added and the mixture was extracted with ether. After evaporation of the solvent the residue was purified by flash-chromatography (eluent toluene/acetone 4/1) and crystallized by ligroin. This yields 1.9 g of a product with the following characteristics: m.p.125–126° C.; $^1$H NMR δ: 2.4 (s, 3H), 2.52 (m, 4H), 3.3 (m, 2H), 3.7 (m, 4H), 4.78 (m, 2H), 6.16–7.54(m, 4H).

Example 27

7-(4-Diethylaminobut-2-yn)-oxy-4-methylcoumarin (See Accompanying Formula Drawing VIB 94)

A solution of formaldehyde (1 ml), morpholine (0.73 g, 0.01 mol) and CuSO$_4$ (0.2 g) in EtOH/H$_2$O (40 mL) was added to a solution of propynyloxy derivative (2.14 g, 0.01 mol) in EtOH/H$_2$O (40 mL). H$_2$SO$_4$ was added until pH 8 and the mixture was refluxed 24 h. NH$_3$ (60 mL) was added and the mixture was extracted with ether. After evaporation of the solvent the residue was purified by flash-chromatography (eluent: toluene/acetone 4/1) and crystallized by ligroin. This yields 1.9 g of a product with the following characteristics: m.p. 108–110° C.; $^1$H NMR δ: 1.04 (t, 6H), 2.42 (s, 2H), 2.5 (q, 4H), 3.7 (m, 2H), 4.8 (m, 2H), 6.18–7.57(m, 4H).

Example 28

1-(4-Morpholinobut-2-yn)-oxyxanthone (See Accompanying Formula Drawing VIB 99)

A solution of formaldehyde (1 ml), morpholine (0.87 g, 0.01 mol) and CuSO$_4$ (0.2 g) in EtOH/H$_2$O (40 mL) was added to a solution of propynyloxy derivative (2.5 g, 0.01 mol) in EtOH/H$_2$O (40 mL). H$_2$SO$_4$ was added until pH 8 and the mixture was refluxed 24 h. NH$_3$ (60 mL) was added and the mixture was extracted with ether. After evaporation of the solvent the residue was purified by flash-chromatography (eluent: toluene/acetone 4/1) and crystallized by ligroin. This yields 1.8 g of a product with the following characteristics: m.p. 98–101° C.; $^1$H NMR δ: 2.53 (m, 4H), 3.34 (m, 2H), 3.73 (m, 4H), 4.98 (m, 2H), 6.98–8.33 (m, 7H).

Example 29

1-(4-Diethylaminobut-2-yn)-oxyxanthone (See Accompanying Formula Drawing VIB 98)

A solution of formaldehyde (1 ml), diethylamine (0.73 g, 0.01 mol) and CuSO$_4$ (0.2 g) in EtOH/H$_2$O (40 mL) was added to a solution of propynyloxy derivative (2.5 g, 0.01 mol) in EtOH/H₂O (40 mL). H2SO4 was added until pH 8 and the mixture was refluxed 24 h. NH₃ (60 mL) was added and the mixture was extracted with ether. After evaporation of the solvent the residue was purified by flash-chromatography (eluent: toluene/acetone 4/1) and crystallized by ligroin. This yields 0.64 g of a product with the following characteristics: m.p. 70–72° C.; ¹H NMR δ: 1.02 (t, 6H), 2.5 (q, 4H), 3.45 (m, 2H), 4.96 (m, 2H), 6.98–8.33 (m, 7H).

Example 30

2-(4-Morpholinobut-2-yn)oxyxanthone (see Accompanying Formula Drawing VIB 101)

A solution of formaldehyde (1 ml), morpholine (0.87 g, 0.01 mol) and CuSO₄ (0.2 g) in EtOH/H₂O (40 mL) was added to a solution of propynyloxy derivative (2.5 g, 0.01 mol) in EtOH/H₂O (40 mL). H₂SO₄ was added until pH 8 and the mixture was refluxed 24 h. NH₃ (60 mL) was added and the mixture was extracted with ether. After evaporation of the solvent the residue was purified by flash-chromatography (eluent: toluene/acetone 4/1) and crystallized by ligroin. This yields 1.8 g of a product with the following characteristics: m.p. 105–106° C.; ¹H NMR δ: 2.53 (m, 4H), 3.33 (m,2H), 3.7 (m, 4H), 4.84 (m, 2H), 7.39–7.83 (m, 7H).

Example 31

2-(4-Diethylaminobut-2-yn)-oxyxanthone (See Accompanying Formula Drawing VIB 100)

A solution of formaldehyde (1 ml), diethylamine (0.73 g, 0.01 mol) and CuSO₄ (0.2 g) in EtOH/H₂O (40 mL) was added to a solution of propynyloxy derivative (2.5 g, 0.01 mol) in EtOH/H₂O (40 mL). H2SO4 was added until pH 8 and the mixture was refluxed 24 h. NH₃ (60 mL) was added and the mixture was extracted with ether. After evaporation of the solvent the residue was purified by flash-chromatography (eluent: toluene/acetone 4/1) and crystallized by ligroin. This yields 0.64 g of a product with the following characteristics: m.p. 66–68° C.; ¹H NMR δ: 1.08 (t, 6H), 2.54 (q, 4H), 3.5 (m, 2H), 4.86 (m, 2H), 7.35–8.38 (m, 7H).

Example 32

3-(4-Morpholinobut-2-yn)-oxyxanthone (see Accompanying Formula Drawing VIB 96)

A solution of formaldehyde (1 ml), morpholine (0.87 g, 0.01 mol) and CuSO₄ (0.2 g) in EtOH/H₂O (40 mL) was added to a solution of propynyloxy derivative (2.5 g, 0.01 mol) in EtOH/H₂O (40 mL). H₂SO₄ was added until pH 8 and the mixture was refluxed 24 h. NH₃ (60 mL) was added and the mixture was extracted with ether. After evaporation of the solvent the residue was purified by flash-chromatography (eluent: toluene/acetone 4/1) and crystallized by ligroin. This yields 1.5 g of a product with the following characteristics: m.p. 126–128° C.; ¹H NMR δ: 2.56 (m, 4H), 3.4 (m, 2H), 3.7 (m, 4H), 4.86 (m, 2H), 6.97–8.37 (m, 7H).

Biological Evaluation

Compounds VIB 16, VIB 94, VIB 99 and VIB 100 were tested for their cytotoxicity against drug-resistant cancer cells, both alone, and in combination with paclitaxel. The results of these studies are shown below.

When tested alone these compounds were found to possess relatively low cytotoxicity (IC₅₀>30 μM) against drug-resistant cancer cells.

The compounds were then evaluated in combination with paclitaxel for their cytostatic activity against the drug-resistant breast cancer cells MDA435/LCC6-MDR. In the experiments, the compounds were used in combination with paclitaxel, the paclitaxel being at a concentration of 1 μM. The IC₅₀ of paclitaxel decreases by 2-4 fold when used in combination with each of compounds, i.e. from 426 nM to 210–110 nM compared with paclitaxel alone. Consequently, in the presence of these compounds, paclitaxel can recover its excellent inhibitory activity against the drug-resistant cancer cells.

TABLE 1

| Compound | IC₅₀/nM | % Reduction in IC₅₀ of paclitaxel |
| --- | --- | --- |
| Paclitaxel | 426 | — |
| VIB 16 + Paclitaxel | 136 | 67 |
| VIB 94 + Paclitaxel | 210 | 50 |
| VIB 99 + Paclitaxel | 200 | 53 |
| VIB 100 + Paclitaxel | 110 | 70 |

Experimental

The treatment consisted of concurrent exposure of MDA-435/LCC-MDR cells to paclitaxel in the presence or absence of the compounds reversing agent (1 μM) for 72 h in vitro. Assessment of cytotoxicity, i.e. cell growth inhibition, was determined according to the methods of Skehan, et al. as discussed in J. Nat. Cancer Inst., 82, 1107,1990.

Briefly, cells were plated between 400 and 1200 cells/well in 96 well plates and incubated at 37° C. for 15–18 h prior to drug addiction to allow attachment of cells. Compounds were solubilzed in 100% DMSO and further diluted in RPMI-1640 containing 10 mM HEPES. After a 72 h incubation, 100 μl of ice-cold 50% TCA was added to each well and incubated for 1 h at 4° C. Plates were then washed 5 times with tap water to remove TCA, low-molecular weight metabolites and serum proteins. Sulforhodamine B (RSB) (0.4%, 50 μl) was added to each well. Following a five minute incubation at room temperature, plates were rinsed 5 times with 0.1% acetic acid and air dried. Bound dye was solubilized with 10 mM Tris Base (pH 10.5) for 5 min on a gyratory shaker. Optical density was measured at 570 nm.

VIB 15

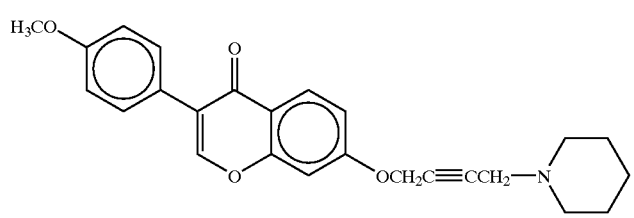

-continued
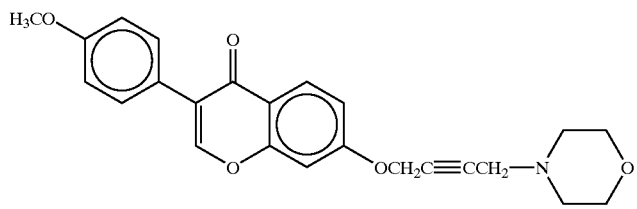
VIB 17
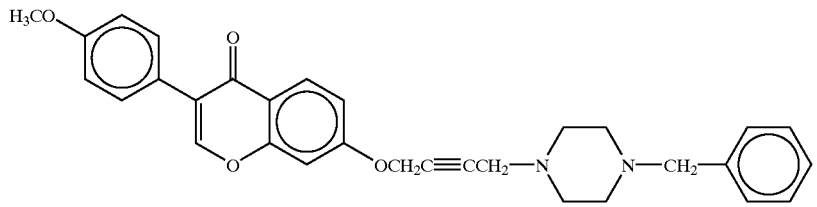
VIB 16
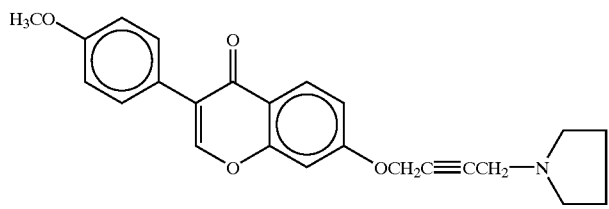
VIB 91
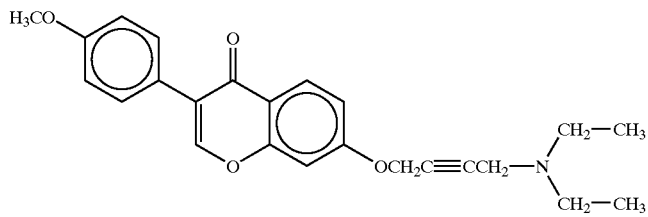
VIB 90
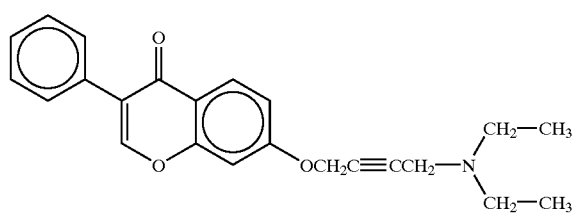
VIB 92
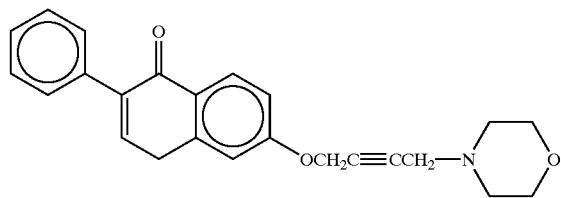
VIB93
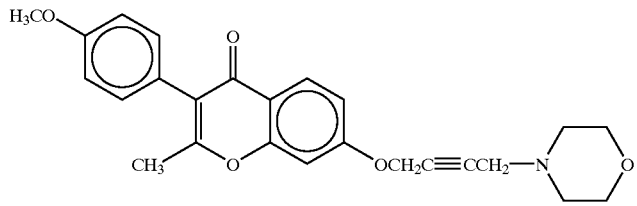
VIB 105

-continued
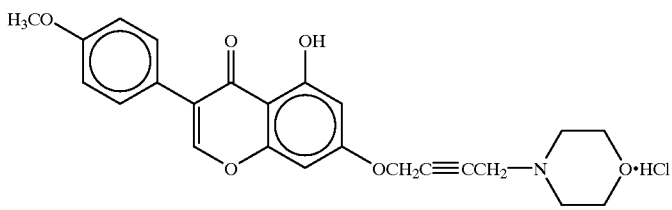
VIB 102
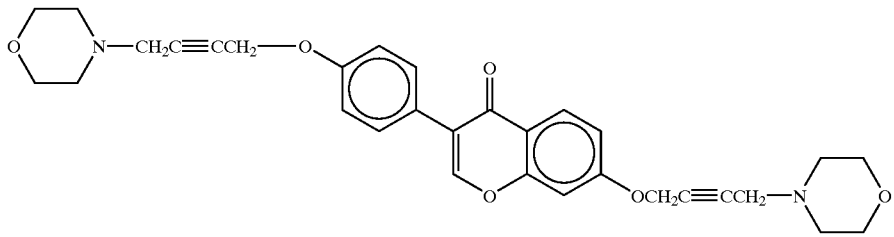
VIB 97
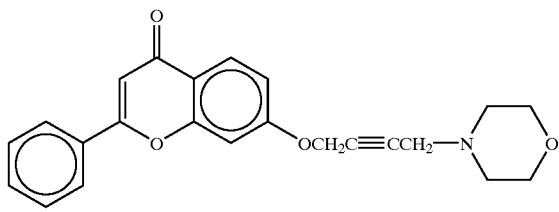
VIB 103
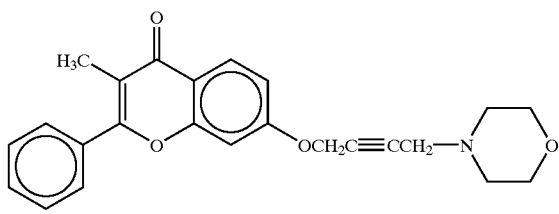
VIB 104
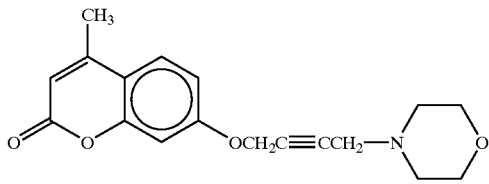
VIB 95
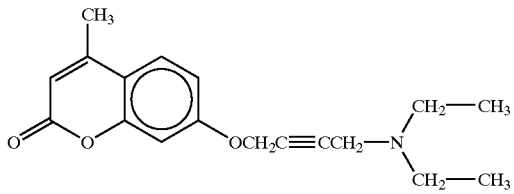
VIB 94
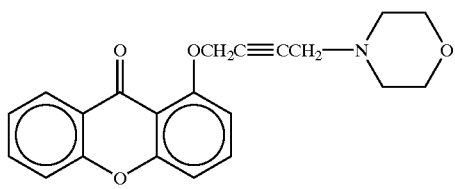
VIB 99

-continued

VIB 98
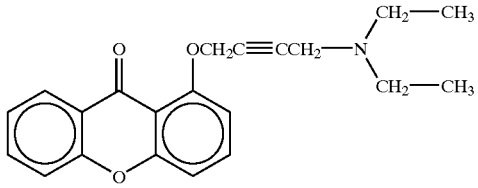

VIB 101
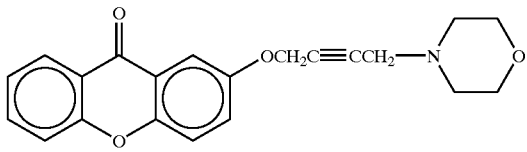

VIB 100
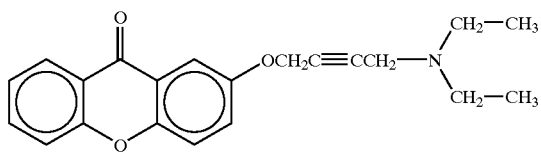

VIB 96
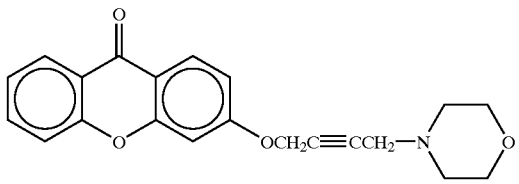

What is claimed is:

1. A compound of Formula (I):

$$Z-OCH_2-C\equiv CCH_2-NRR^1 \quad (I)$$

or a pharmaceutically acceptable salt or solvate thereof wherein

R and $R^1$ are the same or different and each represents a $C_{1-6}$ alkyl, a carbocyclic group containing from 5 to 10 ring atoms or two rings with each ring containing 5 or 6 ring atoms, or R and $R^1$ taken together with the nitrogen atom to which they are attached form a four- to eight-membered heterocyclic ring which may contain one or more additional heteroatoms selected from N, O or S, said heterocyclic ring being optionally substituted with a $C_{1-4}$ alkyl group or a benzyl group;

Z represents:

(A)
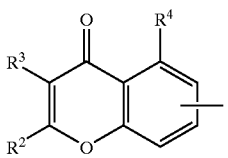

wherein $R^2$ and $R^3$ are each independently selected from:
(i) hydrogen;
(ii) a substituted or unsubstituted, aromatic or non-aromatic carbocyclic or heterocyclic group containing from 5 to 10 ring atoms or two rings with each ring containing 5 or 6 ring atoms, wherein the heterocyclic group comprises a heteroatom selected from N, O and S, and wherein the carbocyclic or heterocyclic group can be substituted with one or more substituents being independently selected from the group consisting of: (a) Cl, (b) Br, (c) F, (d) OH, (e) $NO_2$, (f) $CF_3$, (g) $C_{1-4}$ alkyl, (h) $SCH_3$, (i) $NHCOCH_3$, (j) $N(R^6)(R^8)$ wherein $R^6$ and $R^8$, are the same or different and each represents H or a $C_{1-4}$ alkyl, (k) $OR^{10}$ wherein $R^{10}$ represents H or $C_{1-6}$ alkyl which may be saturated or unsaturated and may be unsubstituted or substituted with the group $NRR^1$ wherein R and $R^1$ is as defined above, and (l) $OCOR^{11}$ wherein $R^{11}$ represents H or $C_{1-4}$ alkyl,
(iii) Cl;
(iv) Br;
(v) F;
(vi) OH;
(vii) $NO_2$;
(viii) a saturated or unsaturated $C_{1-6}$ straight or branched hydrocarbyl group which may be unsubstituted or substituted with from 1 to 3 substituents selected from Cl, Br, F, OMe, $NO_2$ and $CF_3$;
(ix) $NHCOCH_3$;
(x) $N(R^6)(R^8)$, wherein $R^6$ and $R^8$ are defined above;
(xi) $SR^{10}$, wherein $R^{10}$ is defined above;
(xii) $OR^{10}$ wherein $R^{10}$ is defined above; and
(xiii) $OCOR^{11}$ wherein $R^{11}$ is defined above; or $R^2$ and $R^3$ taken together with the carbon atoms to which they are attached form a saturated or unsaturated carbocyclic or heterocyclic ring having 5 or 6 ring atoms, wherein the heterocyclic group comprises a heteroatom selected from N, O and S, and wherein the carbocyclic or heterocyclic group can be substituted with one or more substituents being independently selected from the group consisting of Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$ wherein $R^6$, $R^8$, $R^{10}$ and $R^{11}$ are as defined above; and $R^4$ represents hydrogen, or $OR^{10}$ wherein $R^{10}$ is as defined above; or (B)

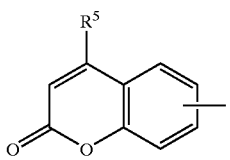

wherein
$R^5$ hydrogen or a $C_{1-6}$ straight or branched hydrocarbyl group which may be unsubstituted or substituted with from 1 to 3 substituents selected from Cl, Br, F, OMe, $NO_2$ and $CF_3$;
with the proviso that when Z represents

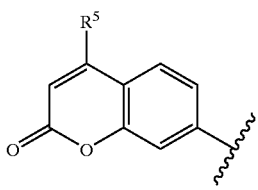

and $R^5$ is hydrogen or an alkyl group containing up to 4 carbon atoms then R and $R^1$ cannot be an alkyl groups that contains from 1 to 4 carbon atoms or R and $R^1$ when taken together with the nitrogen atom to which they are attached cannot form a saturated heterocyclic amino radical containing 5 to 7 ring members.

2. The compound of claim 1 having the structure (IA'):

(IA')

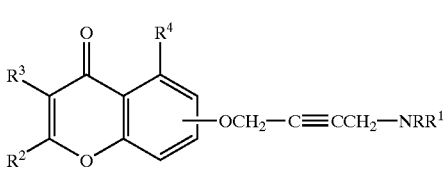

wherein
$R^2$ and $R^3$ are each independently selected from:
(i) hydrogen;
(ii) a substituted or unsubstituted, aromatic or non aromatic, carbocyclic or heterocyclic group containing from 5 to 10 ring atoms or two rings with each ring containing 5 or 6 ring atoms, and wherein the carbocyclic or heterocyclic group can be substituted with one or more substituents being independently selected from the group consisting of: Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$, wherein $R^6$, $R^8$, $R^{10}$ and $R^{11}$ are the same or different and each represents H or $C_{1-4}$ alkyl;
(iii) Cl;
(iv) Br;
(v) F;
(vi) OH;
(vii) $NO_2$;
(viii) a saturated or unsaturated $C_{1-6}$ straight or branched hydrocarbyl group which may be unsubstituted or substituted with between 1 and 3 substituents selected from Cl, Br, F, OMe, $NO_2$, and $CF_3$;
(ix) $NHCOCH_3$;
(x) $N(R^6)(R^8)$, wherein $R^6$ and $R^8$ are as defined above;
(xi) $SR^{10}$, wherein $R^{10}$ is defined above;
(xii) $OR^{10}$, wherein $R^{10}$ is defined above; and
(xiii) $OCOR^{11}$ wherein $R^{11}$ is defined above; or
$R_2$ and $R_3$ taken together with the carbon atoms to which they are attached form a saturated or unsaturated carbocyclic or heterocyclic ring having 5 or 6 ring atoms, wherein the heterocycle comprises a heteroatom selected from N, O and S, and wherein the carbocyclic or heterocyclic group can be substituted with one or more substituents being independently selected from the group consisting of Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$ wherein $R^6$, $R^8$, $R^{10}$ and $R^{11}$ are as defined above; and
$R^4$ represents hydrogen, or $OR^{10}$ wherein $R^{10}$ is as defined above.

3. A compound according to claim 2, wherein R, $R^1$ and $R^4$ are as defined in claim 1
$R^2$ and $R^3$ are each independently selected from:
(i) hydrogen;
(ii) a substituted or unsubstituted, aromatic or non-aromatic, carbocyclic or heterocyclic group containing from 5 to 10 ring atoms or two rings with each ring containing 5 or 6 ring atoms, wherein the heterocyclic ring comprises a heteroatom selected from N, O and S, and wherein the carbocyclic or heterocyclic group can be substituted with one or more substituents being independently selected from the group consisting of: (a) Cl, (b) Br, (c) F, (d) OH, (e) $NO_2$, (f) $CF_3$, (g) $C_{1-4}$ alkyl, (h) $SCH_3$, (I) $NHCOCH_3$, (j) $N(R^6)(R^8)$ wherein $R^6$ and $R^8$ are the same or different and each represents H or $C_{1-4}$ alkyl, (k) $OR^{10}$ wherein $R^{10}$ represents H or $C_{1-6}$ alkyl which may be saturated or unsaturated and unsubstituted or substituted with the group $NRR^1$ wherein R and $R^1$ is as defined above, and (1) $OCOR^{11}$ wherein $R^{11}$ represents H or $C_{1-4}$ alkyl;
(iii) Cl;
(iv) Br;
(v) F;
(vi) OH;
(vii) $NO_2$;
(viii) a saturated or unsaturated $C_{1-6}$ straight or branched hydrocarbyl group which may be unsubstituted or substituted with between 1 and 3 substituents selected from Cl, Br, F, OMe, $NO_2$, and $CF_3$;
(ix) $NHCOCH_3$;
(x) $N(R^6)(R^8)$, wherein $R^6$ and $R^8$ are as defined in claim 1;
(xi) $SR^{10}$, wherein $R^{10}$ is as defined in claim 1;
(xii) $OR^{10}$, wherein $R^{10}$ is as defined in claim 1; and
(xiii) $OCOR^{11}$, wherein $R^{11}$ is as defined in claim 1.

4. The compound of claim 1, wherein $R^2$ and $R^3$ are hydrogen.

5. The compound of claim 1, wherein one of $R^1$ or $R^2$ is hydrogen, and the other is selected from the group consisting of:

(i) a substituted or unsubstituted, aromatic or non-aromatic, carbocyclic or heterocyclic group containing from 5 to 10 ring atoms or two rings with each ring containing 5 or 6 ring atoms, wherein the heterocycle comprises a heteroatom selected from N, O and S, and wherein the carbocyclic or heterocyclic group can be substituted with one or more substituents being independently selected from the group consisting of: Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$, wherein $R^8$, $R^8$, $R^{10}$ and $R^{11}$ are the same or different and each represents H or $C_{1-4}$ alkyl;
(ii) Cl;
(iii) Br;
(iv) F;
(v) OH;
(vi) $NO_2$;
(vii) a saturated or unsaturated $C_{1-4}$ straight or branched hydrocarbyl group which may be unsubstituted or substituted with from 1 to 3 substituents selected from Cl, Br, F, OMe, $NO_2$ and $CF_3$;
(viii) $NHCOCH_3$;
(ix) $N(R^6)(R^8)$, wherein $R^6$ and $R^8$ are as defined in claim 1;
(x) $SR^{10}$, wherein $R^{10}$ is as defined in claim 1;
(xi) $OR^{10}$, wherein $R^{10}$ is as defined in claim 1;
(xii) $OCOR^{11}$, wherein $R^{11}$ is as defined in claim 1.

6. The compound of claim 1, wherein $R^2$ is hydrogen and $R^3$ is selected from the group consisting of:
(i) a substituted or unsubstituted, aromatic or non-aromatic, carbocyclic or heterocydlic group containing from 5 to 10 ring atoms or two rings with each ring containing 5 or 6 ring atoms, wherein the heterocycle comprises a heteroatom selected from N, O and S, and wherein the carbocyclic or heterocyclic group can be substituted with one or more substituents being independently selected from the group consisting of: Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$, wherein $R^6$, $R^8$, $R^{10}$ and $R^{11}$ are the same or different and each represents H or $C_{1-4}$ alkyl;
(ii) Cl;
(iii) Br;
(iv) F;
(v) OH;
(vi) $NO_2$;
(vii) a saturated or unsaturated $C_{1-4}$ straight or branched hydrocarbyl group which may be unsubstituted or substituted with from 1 to 3 substituents selected from Cl, Br, F, OMe, $NO_2$ and $CF_3$;
(viii) $NHCOCH_3$;
(ix) $N(R^6)(R^8)$, wherein $R^6$ and $R^8$ are as defined in claim 1;
(x) $SR^{10}$, wherein $R^{10}$ is as defined in claim 1;
(xi) $OR^{10}$, wherein $R^{10}$ is as defined in claim 1;
(xii) $OCOR^{11}$, wherein $R^{11}$ is as defined in claim 1.

7. The compound of claim 5, wherein $R^3$ is hydrogen and $R^2$ is selected from the group consisting of:
(i) a substituted or unsubstituted, aromatic or non-aromatic, carbocyclic or heterocyclic group containing from 5 to 10 ring atoms or two rings with each ring containing 5 or 6 ring atoms, wherein the heterocycle comprises a heteroatom selected from N, O and S, and wherein the carbocyclic or heterocyclic group can be substituted with one or more substituents being independently selected from the group consisting of: Cl, Br, F, OH, $NO_2$, $CF_3$, $C_{1-4}$ alkyl, $SCH_3$, $NHCOC$ $H_3$, $N(R^6)(R^8)$, $OR^{10}$ and $OCOR^{11}$, wherein $R^6$, $R^8$, $R^{10}$ and $R^{11}$ are the same or different and each represents H or lower $C_{1-4}$ alkyl;
(ii) Cl;
(iii) Br;
(iv) F;
(v) OH;
(vi) $NO^2$
(vii) a saturated or unsaturated $C_{1-4}$ straight or branched hydrocarbyl group which may be unsubstituted or substituted with from 1 to 3 substituents selected from Cl, Br, F, OMe, $NO_2$ and $CF_3$;
(viii) $NHCOCH_3$;
(ix) $N(R^6)(R^8)$, wherein $R^6$ and $R^8$ are as defined in claim 1;
(x) $SR^{10}$, wherein $R^{10}$ is as defined in claim 1;
(xi) $OR^{10}$, wherein $R^{10}$ is as defined in claim 1;
(xii) $OCOR^{11}$, wherein $R^{11}$ is as defined in claim 1.

8. The compound of claim 5, wherein $R^2$ represents a substituted or unsubstituted, aromatic or non-aromatic, carbocyclic or heterocyclic group containing from 5 to 10 ring atoms or two rings with each ring containing 5 or 6 ring atoms, wherein the heterocycle comprises a heteroatom selected from N, O and S, and wherein the carbocyclic or heterocyclic group can be substituted with one or more substituents being independently selected from the group consisting of: Cl, Br, F, OH, $NO_2$, $CF_3$, $C_{1-4}$ alkyl, $SCH_3$, $NHCOC$ $H_3$, $N(R^6)(R^8)$, $OR^{10}$ and $OCOR^{11}$, wherein $R^6$, $R^8$, $R^{10}$ and $R^{11}$ are as defined in claim 1.

9. The compound of claim 6, wherein $R^3$ represents a substituted or unsubstituted, aromatic or non-aromatic, carbocyclic or heterocyclic group containing from 5 to 10 ring atoms or two rings with each ring containing 5 or 6 ring atoms, and wherein the heterocycle comprises a heteroatom selected from N, O and S, and wherein the carbocyclic or heterocyclic group can be substituted with one or more substituents being independently selected from the group consisting of: Cl, Br, F, OH, $NO_2$, $CF_3$, $C_{1-4}$ alkyl, $SCH_3$, $NHCOCH_3$, $N(R^6)(R^8)$, $OR^{10}$ and $OOOR^{11}$, wherein $R^6$, $R^8$, $R^{10}$ and $R^{11}$ are as defined in claim 3.

10. A compound according to claim 3, wherein $R^3$ is selected from the group consisting of H, Cl, Br, F, OH, $NO_2$, a saturated or unsaturated $C_{1-4}$ straight or branched hydrocarbyl group which may be unsubstituted or substituted with from 1 to 3 substituents selected from Cl, Br, F, OMe, $NO_2$ and $CF_3$, $NHOOCH_3$, $N(R^6)(R^8)$, $SR^{10}$, $OR^{10}$, and $OCOR^{11}$ wherein $R^6$, $R^8$, $R^{10}$ and $R^{11}$ are as defined in claim 3.

11. The compound of claim 3, wherein $R^2$ is selected from the group consisting of H, Cl, Br, F, OH, $NO_2$, a saturated or unsaturated $C_{1-6}$ straight or branched hydrocarbyl group which may be unsubstituted or substituted with from 1 to 4 substituents selected from Cl, Br, F, OMe, $NO_2$ and $CF_3$, $NHCOCH_3$, $N(R^6)(R^8)$, $SR^{10}$, $OR^{10}$, and $OCOR^{11}$ wherein $R^6$, $R^8$, $R^{10}$ and $R^{11}$ are as defined in claim 3.

12. The compound of claim 1, wherein the substituents on the carbocyclic or heterocyclic group are independently selected from OH or $OR^{10}$ wherein $R^{10}$ is as defined in claim 1.

13. The compound of claim 1, wherein one of $R^2$ or $R^3$ represents a phenyl or a phenyl substituted with from 1 to 3 OH or $OR^{10}$ groups.

14. The compound of claim 12, wherein $R^{10}$ represents methyl or

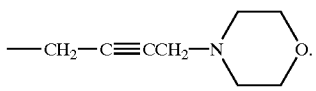

15. The compound of claim 1, wherein one of $R^2$ or $R^3$ is H or a $C_{1-6}$ straight or branched hydrocarbyl group.

16. The compound of claim 15, wherein one of $R^2$ or $R^3$ is methyl.

17. The compound of claim 2, having the structure (IA"):

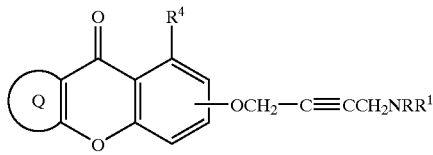

(IA")

wherein
R, $R^1$, and $R^4$ are as defined in claim 1; and
$R^2$ and $R^3$ taken together represent ring Q, wherein ring Q is a saturated or unsaturated carbocyclic or heterocyclic ring having 5 or 6 ring atoms, wherein the heterocycle comprises a heteroatom selected from N, O and S, and wherein the carbocyclic or heterocyclic group can be substituted with one or more substituents being independently selected from the group consisting of Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$, wherein $R^6$, $R^8$, $R^{10}$ and $R^{11}$ are as defined as in claim 1.

18. The compound of claim 17, wherein ring Q is a carbocyclic or heterocyclic aromatic ring.

19. The compound of claim 18, wherein ring Q is a benzene or pyridine ring.

20. The compound of claim 1 having a structure selected from the group consisting of

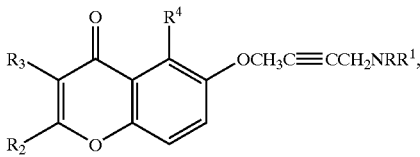

(IAX)

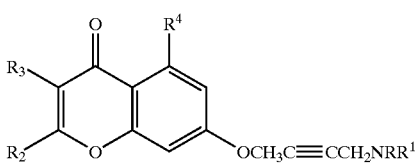

(IAY)

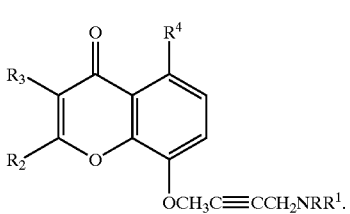

(IAZ)

wherein R, $R^1$, $R^2$, $R^3$ and R' are as defined in claim 1.

21. The compound of claim 20 having the structure (1AX).

22. The compound of claim 20 having the structure (1AY).

23. The compound of claim 20 having the structure (1AZ).

24. The compound of claim 1, wherein $R^4$ represents H, OH, or $OCH_3$.

25. A compound of claim 1 having the structure (IB):

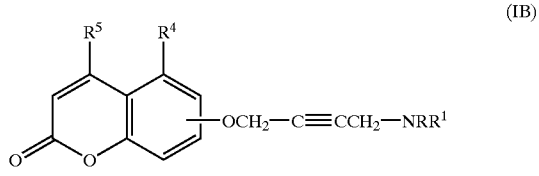

(IB)

wherein $R^5$ is H or a $C_{1-6}$ straight or branched hydrocarbyl group which may be unsubstituted or substituted with from 1 to 3 substituents selected from Cl, Br, F, OMe, $NO_2$ and $CF_3$.

26. The compound of claim 25 having a structure selected from the group consisting of:

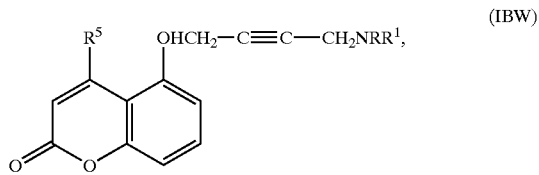

(IBW)

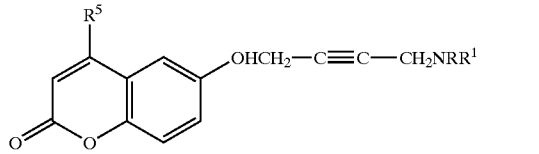

(IBX)

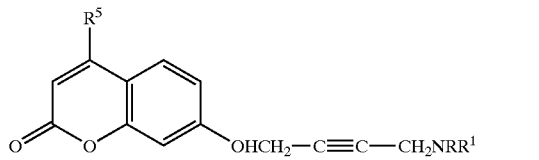

(IBY)

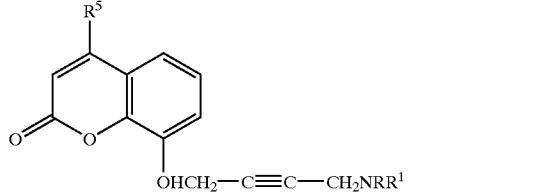

(IBZ)

wherein R, $R^1$, and $R^5$ are as defined in claim 1.

27. A compound according to claim 26 having the structure (1BW).

28. A compound according to claim 26 having the structure (1BX).

29. A compound according to claim 26 having the structure (1BY).

30. A compound according to claim 26 having the structure (1BZ).

31. The compound of claim 25, wherein $R^5$ represents H or methyl.

32. The compound of claim 1, wherein R and $R^1$ are the same or different and each represents a $C_{1-4}$ alkyl group or a $C_{5-8}$ cycloalkyl group.

33. The compound of claim 1 wherein R and $R^1$ taken together with the nitrogen atom to which they are attached form a four to eight membered heterocyclic ring.

34. The compound of claim 32, wherein R and $R^1$ are the same or different and each represents methyl, ethyl, propyl, cyclopropyl or a cyclohexyl group.

35. The compound of claim 33, wherein R and $R^1$ taken together with the nitrogen atom to which they are attached form a pyrrolidine, piperidine, N-methylpiperidine, N-benzylpiperidine, or morpholine group.

36. A compound selected from:

7-(4-piperidinobut-2-yn)oxy-4'-methoxyisoflavone, 7-(4-morpholinobut-2-yn)oxy-4'-methoxyisoflavone, 7-[4-(4-benzylpiperazin-1-yl)but-2-yn]oxy-41-methoxyisoflavone, 7-(4-pyrrolidinobut-2-yn)oxy-4--methoxyisoflavone, 7-(4-diethylaminobut-2-yn)oxy-4'-methoxyisoflavone, 7-(4-diethylaminobut-2-yn)oxyisoflavone, 7-(4-morpholinobut-2-yn)oxyisoflavone, 7-(4-morpholinobut-2-yn)oxy-2-methyl-4-methoxyisoflavone, 7-(4-morpholinobut-2-yn)oxy-5-hydroxy-4-methoxyisoflavone, 7-(4-bis-4-morpholinobut-2-yn)oxyisoflavone, 7-(4-morpholinobut-2-yn)oxyflavone, 7-(4-morpholinobut-2-yn)oxy-3-methylflavone, 7-(4-morpholinobut-2-yn)oxy-4-methylcoumarin, 7-(4-diethylaminobut-2-yn)oxy-4-methylcoumarin, 1-(4-morpholinobut-2-yn)oxyxanthone, 1-(4-diethylaminobut-2-yn)oxyxanthone, 2-(4-morpholinobut-2-yn)oxyxanthone, 2-(4-diethylaminobut-2-yn)oxyxanthone, and 3-(4-morpholinobut-2-yn)oxyxanthofle.

37. A method of treating cancer in a patient or modulating multiple drug resistance in a patient receiving cancer chemotherapy comprising administering to the patient a compound of Formula I:

or a pharmaceutically acceptable salt or solvate thereof wherein

R and $R^1$ are the same or different and each represents a $C_{1-6}$ alkyl, a carbocyclic group containing from 5 to 10 ring atoms or two rings with each ring containing 5 or 6 ring atoms, or R and $R^1$ taken together with the nitrogen atom to which they are attached form a four- to eight-membered heterocyclic ring which may contain one or more additional heteroatoms selected from N, O or S, said heterocyclic ring being optionally substituted with a $C_{1-4}$ alkyl group or a benzyl group;

Z represents:

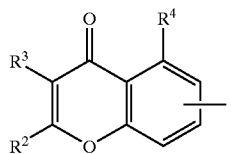

(A)

wherein $R^2$ and $R^3$ are each independently selected from:
(i) hydrogen;
(ii) a substituted or unsubstituted, aromatic or non-aromatic carbocyclic or heterocyclic group containing from 5 to 10 ring atoms or two rings with each ring containing 5 or 6 ring atoms, wherein the heterocyclic group comprises a heteroatom selected from N, O and S, and wherein the carbocyclic or heterocyclic group can be substituted with one or more substituents being independently selected from the group consisting of: (a) Cl, (b) Br, (c) F, (d) OH, (e) $NO_2$, (f) $CF_3$, (g) $C_{1-4}$ alkyl, (h) $SCH_3$, (i) $NHCOCH_3$, (j) $N(R^6)(R^8)$ wherein $R^6$ and $R^8$, are the same or different and each represents H or a $C_{1-4}$ alkyl, (k) $OR^{10}$ wherein R represents H or $C_{1-6}$ alkyl which may be saturated or unsaturated and may be unsubstituted or substituted with the group $NRR^1$ wherein R and $R^1$ is as defined above, and (1) $OCOR^{11}$ wherein $R^{11}$ represents H or $C_{1-4}$ alkyl,
(iii) Cl;
(iv) Br;
(v) F;
(vi) OH;
(vii) $NO_2$;
(viii) a saturated or unsaturated $C_{1-6}$ straight or branched hydrocarbyl group which may be unsubstituted or substituted with from 1 to 3 substituents selected from Cl, Br, F, OMe, $NO_2$ and $CF_3$;
(ix) $NHCOCH_3$;
(x) $N(R^6)(R^8)$, wherein $R^6$ and $R^8$ are defined above;
(xi) $SR^{10}$, wherein $R^{10}$ is defined above;
(xii) $OR^{10}$ wherein $R^{10}$ is defined above; and
(xiii) $OCOR^{11}$ wherein $R^{11}$ is defined above; or $R^2$ and $R^3$ taken together with the carbon atoms to which they are attached form a saturated or unsaturated carbocyclic or heterocyclic ring having 5 or 6 ring atoms, wherein the heterocyclic group comprises a heteroatom selected from N, O and S, and wherein the carbocyclic or heterocyclic group can be substituted with one or more substituents being independently selected from the group consisting of Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$ wherein $R^6$, $R^8$, $R^{10}$ and $R^{11}$ are as defined above; and $R^4$ hydrogen, or $OR^{10}$ wherein $R^{10}$ is as defined above; or

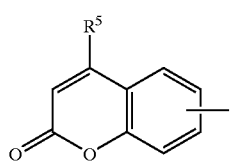

(B)

wherein $R^5$ hydrogen or a $C_{1-6}$ straight or branched hydrocarbyl group which may be unsubstituted or substituted with from 1 to 3 substituents selected from Cl, Br, F, OMe, $NO_2$ and $CF_3$.

38. The method of claim 37, wherein the multiple drug resistance is mediated by P-glycoprotein.

39. A method of treating neoplasms in a patient comprising administering to the patient a compound of Formula (I):

or a pharmaceutically acceptable salt or solvate thereof wherein

R and $R^1$ are the same or different and each represents a $C_{1-6}$ alkyl, a carbocyclic group containing from 5 to 10 ring atoms or two rings with each ring containing 5 or 6 ring atoms, or R and $R^1$ taken together with the nitrogen atom to which they are attached form a four- to eight-membered heterocyclic ring which may contain one or more additional heteroatoms selected from N, O or S, said heterocyclic ring being optionally substituted with a $C_{1-4}$ alkyl group or a benzyl group;

Z represents:

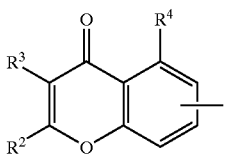

(A)

wherein $R^2$ and $R^3$ are each independently selected from:
(i) hydrogen;
(ii) a substituted or unsubstituted, aromatic or non-aromatic carbocyclic or heterocyclic group containing from 5 to 10 ring atoms or two rings with each ring containing 5 or 6 ring atoms, wherein the heterocyclic group comprises a heteroatom selected from N, O and S, and wherein the carbocyclic or heterocyclic group can be substituted with one or more substituents being independently selected from the group consisting of: (a) Cl, (b) Br, (c) F, (d) OH, (e) $NO_2$, (f) $CF_3$, (g) $C_{1-4}$ alkyl, (h) $SCH_3$, (i) $NHCOCH_3$, (j) $N(R^6)(R^8)$ wherein $R^6$ and $R^8$, are the same or different and each represents H or a $C_{1-4}$ alkyl, (k) $OR^{10}$ wherein R represents H or $C_{1-6}$ alkyl which may be saturated or unsaturated and may be unsubstituted or substituted with the group $NRR^1$ wherein R and $R^1$ is as defined above, and (l) $OCOR^{11}$ wherein $R^{11}$ represents H or $C_{1-4}$ alkyl,
(iii) Cl;
(iv) Br;
(v) F;
(vi) OH;
(vii) $NO_2$;
(viii) a saturated or unsaturated $C_{1-6}$ straight or branched hydrocarbyl group which may be unsubstituted or substituted with from 1 to 3 substituents selected from Cl, Br, F, OMe, $NO_2$ and $CF_3$;
(ix) $NHCOCH_3$;
(x) $N(R^6)(R^8)$, wherein $R^6$ and $R^8$ are defined above;
(xi) $SR^{10}$, wherein $R^{10}$ is defined above;
(xii) $OR^{10}$ wherein $R^{10}$ is defined above; and
(xiii) $OCOR^{11}$ wherein $R^{11}$ is defined above; or
$R^2$ and $R^3$ taken together with the carbon atoms to which they are attached form a saturated or unsaturated carbocyclic or heterocyclic ring having 5 or 6 ring atoms, wherein the heterocyclic group comprises a heteroatom selected from N, O and S, and wherein the carbocyclic or heterocyclic group can be substituted with one or more substituents being independently selected from the group consisting of Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$ wherein $R^6$, $R^8$, $R^{10}$ and $R^{11}$ are as defined above; and $R^4$ represents hydrogen, or $OR^{10}$ wherein $R^{10}$ is as defined above; or

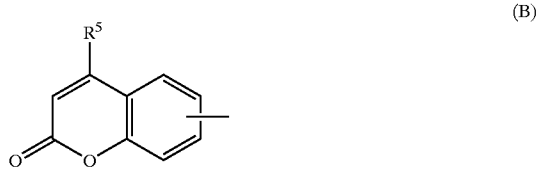

(B)

wherein $R^5$ hydrogen or a $C_{1-6}$ straight or branched hydrocarbyl group which may be unsubstituted or substituted with from 1 to 3 substituents selected from Cl, Br, F, OMe, $NO_2$ and $CF_3$.

40. The method of claim 39, wherein the neoplasms are located in the uterus, ovary or breast.

41. The method of claim 37 wherein the cancer is a paclitaxel- and docetaxel-resistant cancer.

42. The method of claim 39, wherein the compound of Formula (I) is administered as part of combination therapy.

43. The method of claim 42, wherein the compound of Formula (I) is administered in combination with one or more antineoplastic or cytostatic agents.

44. The method of claim 42, wherein the antineoplastic or cytostatic agent is selected from the group consisting of anthracyclines, epipodophyllotoxins, actinomycin D, vinca alkaloids, colchicines, paclitaxel, or docetaxel.

45. A method of treating menopausal disorders or osteoporosis in a patient comprising administering to the patient a compound of Formula I:

(I)

or a pharmaceutically acceptable salt or solvate thereof wherein

R and $R^1$ are the same or different and each represents a $C_{1-6}$ alkyl, a carbocyclic group containing from 5 to 10 ring atoms or two rings with each ring containing 5 or 6 ring atoms, or R and $R^1$ taken together with the nitrogen atom to which they are attached form a four- to eight-membered heterocyclic ring which may contain one or more additional heteroatoms selected from N, O or S, said heterocyclic ring being optionally substituted with a $C_{1-4}$ alkyl group or a benzyl group;

Z represents:

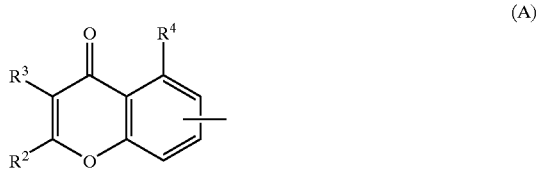

(A)

wherein $R^2$ and $R^3$ are each independently selected from:
(i) hydrogen;
(ii) a substituted or unsubstituted, aromatic or non-aromatic carbocyclic or heterocyclic group containing from 5 to 10 ring atoms or two rings with each ring containing 5 or 6 ring atoms, wherein the heterocyclic group comprises a heteroatom selected from N, O and S, and wherein the carbocyclic or heterocyclic group can be substituted with one or more substituents being independently selected from the group consisting of: (a) Cl, (b) Br, (c) F, (d) OH, (e) $NO_2$, (f) $CF_3$, (g) $C_{1-4}$ alkyl, (h) $SCH_3$, (i) $NHCOCH_3$, (j) $N(R^6)(R^8)$ wherein $R^6$ and $R^8$, are the same or different and each represents H or a $C_{1-4}$ alkyl, (k) $OR^{10}$ wherein $R^{10}$ represents H or $C_{1-6}$ alkyl which may be saturated or unsaturated and may be unsubstituted or substituted with the group $NRR^1$ wherein R and $R^1$ is as defined above, and (l) $OCOR^{11}$ wherein $R^{11}$ represents H or $C_{1-4}$ alkyl,
- (iii) Cl;
- (iv) Br;
- (v) F;
- (vi) OH;
- (vii) $NO_2$;
- (viii) a saturated or unsaturated $C_{1-6}$ straight or branched hydrocarbyl group which may be unsubstituted or substituted with from 1 to 3 substituents selected from Cl, Br, F, OMe, $NO_2$ and $CF_3$;
- (ix) $NHCOCH_3$;
- (x) $N(R^6)(R^8)$, wherein $R^6$ and $R^8$ are defined above;
- (xi) $SR^{10}$ wherein $R^{10}$ is defined above;
- (xii) $OR^{10}$ wherein $R^{10}$ is defined above; and
- (xiii) $OCOR^{11}$ wherein $R^{11}$ is defined above; or $R^2$ and $R^3$ taken together with the carbon atoms to which they are attached form a saturated or unsaturated carbocyclic or heterocyclic ring having 5 or 6 ring atoms, wherein the heterocyclic group comprises a heteroatom selected from N, O and S, and wherein the carbocyclic or heterocyclic group can be substituted with one or more substituents being independently selected from the group consisting of Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$ wherein $R^6$, $R^8$, $R^{10}$ and $R^{11}$ are as defined above; and $R^4$ hydrogen, or $OR^{10}$ wherein $R^{10}$ as defined above; or

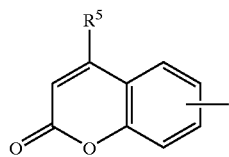

(B)

wherein $R^5$ hydrogen or a $C_{1-6}$ straight or branched hydrocarbyl group which may be unsubstituted or substituted with from 1 to 3 substituents selected from Cl, Br, F, OMe, $NO_2$ and $CF_3$.

46. A pharmaceutical composition comprising a compound of Formula I:

$$Z-OCH_2-C\equiv CCH_2-NRR^1 \qquad (I)$$

or a pharmaceutically acceptable salt or solvate thereof wherein

R and $R^1$ are the same or different and each represents a $C_{1-6}$ alkyl, a carbocyclic group containing from 5 to 10 ring atoms or two rings with each ring containing 5 or 6 ring atoms, or R and $R^1$ taken together with the nitrogen atom to which they are attached form a four- to eight-membered heterocyclic ring which may contain one or more additional heteroatoms selected from N, O or S, said heterocyclic ring being optionally substituted with a $C_{1-4}$ alkyl group or a benzyl group;

Z represents:

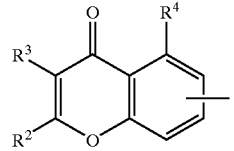

(A)

wherein $R^2$ and $R^3$ are each independently selected from:
- (i) hydrogen;
- (ii) a substituted or unsubstituted, aromatic or non-aromatic carbocyclic or heterocyclic group containing from 5 to 10 ring atoms or two rings with each ring containing 5 or 6 ring atoms, wherein the heterocyclic group comprises a heteroatom selected from N, O and S, and wherein the carbocyclic or heterocyclic group can be substituted with one or more substituents being independently selected from the group consisting of: (a) Cl, (b) Br, (c) F, (d) OH, (e) $NO_2$, (f) $CF_3$, (g) $C_{1-4}$ alkyl, (h) $SCH_3$, (i) $NHCOCH_3$, (j) $N(R^6)(R^8)$ wherein $R^6$ and $R^8$, are the same or different and each represents H or a $C_{1-4}$ alkyl, (k) $OR^{10}$ wherein R represents H or $C_{1-6}$ alkyl which may be saturated or unsaturated and may be unsubstituted or substituted with the group $NRR^1$ wherein R and $R^1$ is as defined above, and (l) $OCOR^{11}$ wherein $R^{11}$ represents H or $C_{1-4}$ alkyl,
- (iii) Cl;
- (iv) Br;
- (v) F;
- (vi) OH;
- (vii) $NO_2$;
- (viii) a saturated or unsaturated $C_{1-6}$ straight or branched hydrocarbyl group which may be unsubstituted or substituted with from 1 to 3 substituents selected from Cl, Br, F, OMe, $NO_2$ and $CF_3$;
- (ix) $NHCOCH_3$;
- (x) $N(R^6)(R^8)$, wherein $R^6$ and $R^8$ are defined above;
- (xi) $SR^{10}$, wherein $R^{10}$ is defined above;
- (xii) $OR^{10}$ wherein $R^{10}$ is defined above; and
- (xiii) $OCOR^{11}$ wherein $R^{11}$ is defined above; or $R^2$ and $R^3$ taken together with the carbon atoms to which they are attached form a saturated or unsaturated carbocyclic or heterocyclic ring having 5 or 6 ring atoms, wherein the heterocyclic group comprises a heteroatom selected from N, O and S, and wherein the carbocyclic or heterocyclic group can be substituted with one or more substituents being independently selected from the group consisting of Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$ wherein $R^6$, $R^8$, $R^{10}$ and $R^{11}$ are as defined above; and $R^4$ represents hydrogen, or $OR^{10}$ wherein $R^{10}$ is as defined above; or

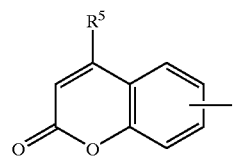

(B)

wherein
R⁵ represents hydrogen or a $C_{1-6}$ straight or branched hydrocarbyl group which may be unsubstituted or substituted with from 1 to 3 substituents selected from Cl, Br, F, OMe, $NO_2$ and $CF_3$;
with the proviso that when Z represents

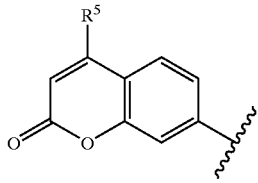

and $R^5$ is hydrogen or an alkyl group containing up to 4 carbon atoms then R and $R^1$ cannot be an alkyl groups that contains from 1 to 4 carbon atoms or R and $R^1$ when taken together with the nitrogen atom to which they are attached cannot form a saturated heterocyclic amino radical containing 5 to 7 ring members; and a pharmaceutically acceptable excipient.

47. The pharmaceutical composition of claim 46 further comprising an antineoplastic or cytostatic agents.

48. The pharmaceutical composition of claim 47 wherein the antineoplastic agent is selected from paclitaxel or docetaxel.

* * * * *

UNITED STATES PATENT AND TRADEMARK OFFICE
CERTIFICATE OF CORRECTION

| | | |
|---|---|---|
| PATENT NO. | : 6,608,089 B2 | Page 1 of 5 |
| APPLICATION NO. | : 10/075628 | |
| DATED | : August 19, 2003 | |
| INVENTOR(S) | : Ezio Bombardelli and Piero Valenti | |

It is certified that error appears in the above-identified patent and that said Letters Patent is hereby corrected as shown below:

On title page item 75

On page 1 in the section titled "Inventors," replace each occurrence of "Milan" with --Milano--.

Item 73

On page 1 in the section titled "Assignee," replace "Milan" with --Milano--.

Column 25, line 10, replace the first occurrence of "$R^8$" with --$R^6$--.

Column 26, line 2, replace the phrase "NHCOC $H_3$" with --$NHCOCH_3$--.

Column 26, line 11, replace the phrase "$NO^2$" with --$NO_2$--.

Column 26, line 34, replace the phrase "NHCOC $H_3$" with --$NHCOCH_3$--.

Column 26, line 45, replace the phrase "$OOOR^{11}$" with --$OCOR^{11}$--.

Column 27, lines 40-64, replace structures (IAX), (IAY), and (IAZ) with

UNITED STATES PATENT AND TRADEMARK OFFICE
CERTIFICATE OF CORRECTION

PATENT NO.        : 6,608,089 B2  
APPLICATION NO. : 10/075628  
DATED              : August 19, 2003  
INVENTOR(S)      : Ezio Bombardelli and Piero Valenti Page 2 of 5

It is certified that error appears in the above-identified patent and that said Letters Patent is hereby corrected as shown below:

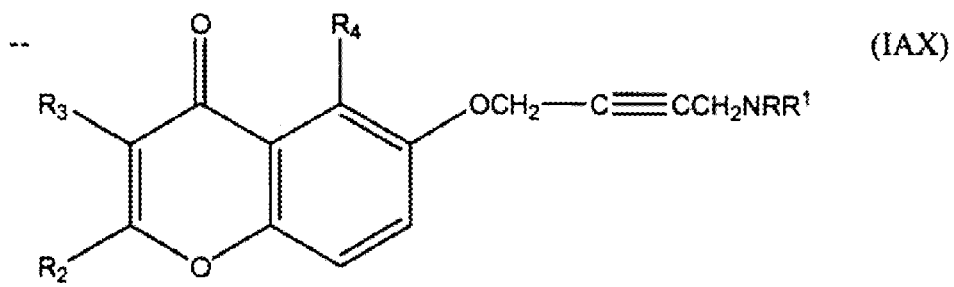

(IAX)

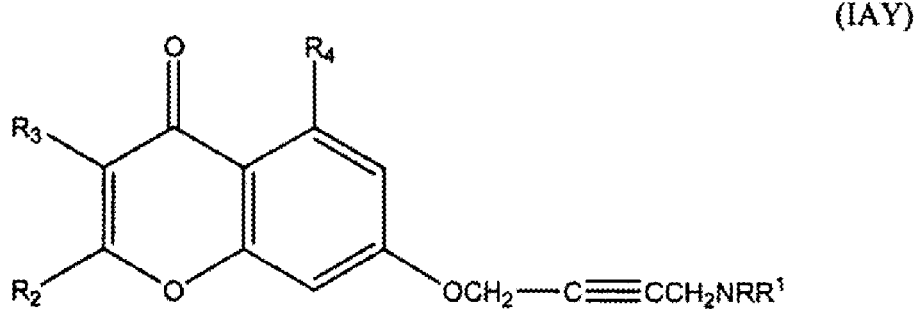

(IAY)

(IAZ)

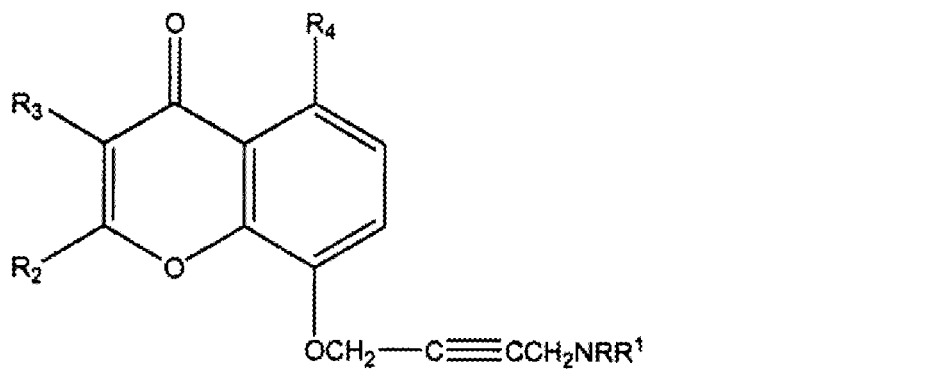

UNITED STATES PATENT AND TRADEMARK OFFICE
CERTIFICATE OF CORRECTION

PATENT NO. : 6,608,089 B2
APPLICATION NO. : 10/075628
DATED : August 19, 2003
INVENTOR(S) : Ezio Bombardelli and Piero Valenti It is certified that error appears in the above-identified patent and that said Letters Patent is hereby corrected as shown below:

Column 28, lines 24-53, replace structures (IBW), (IBX), (IBY), and (IBZ) with

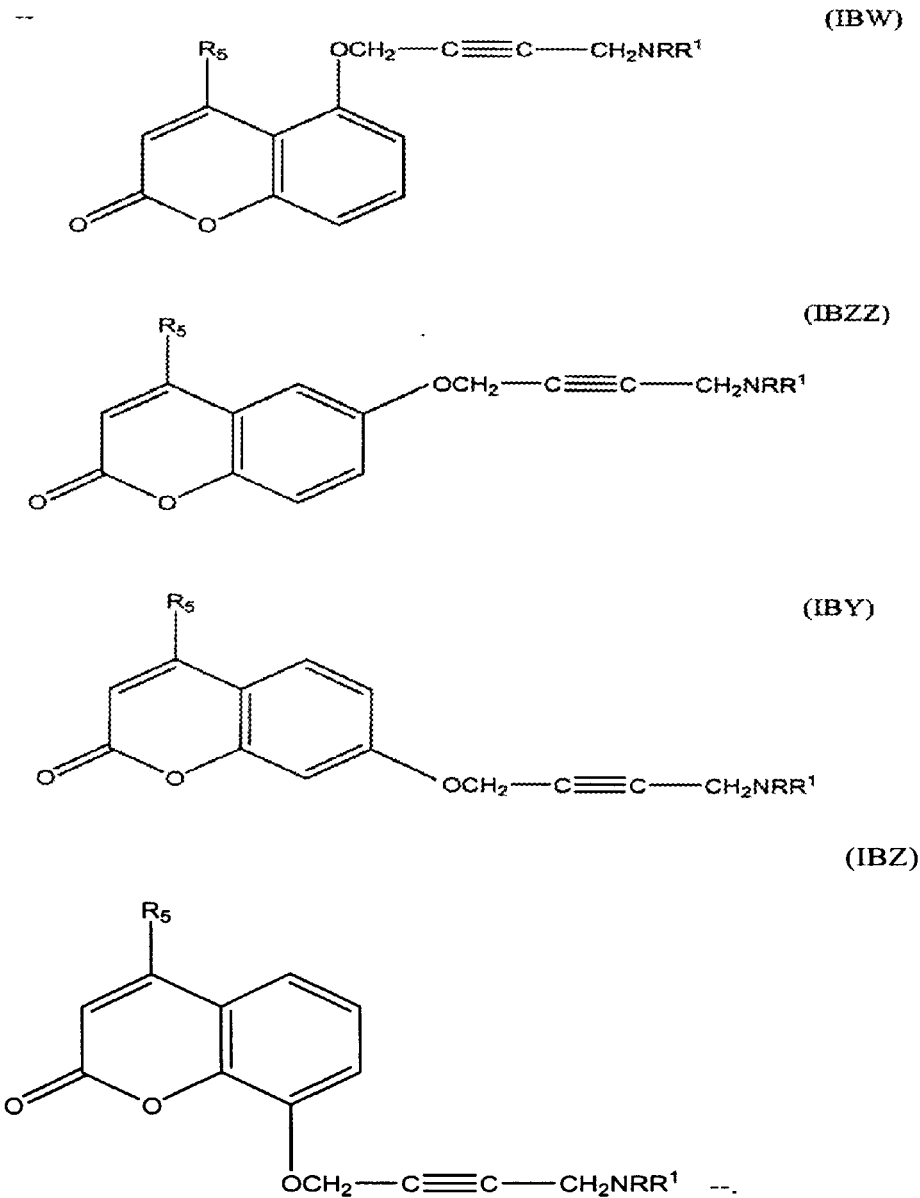

UNITED STATES PATENT AND TRADEMARK OFFICE
CERTIFICATE OF CORRECTION

PATENT NO.         : 6,608,089 B2
APPLICATION NO. : 10/075628
DATED                 : August 19, 2003
INVENTOR(S)       : Ezio Bombardelli and Piero Valenti It is certified that error appears in the above-identified patent and that said Letters Patent is hereby corrected as shown below:

Column 29, lines 15-16 replace "7-[4-(4-benzylpiperazin-1-yl)but-2-yn]oxy-41-methoxyisoflavone" with --7-[4-(4-benzylpiperazin-1-yl)but-2-yn]oxy-4'-methoxyisoflavone--.

Column 29, line 17, replace "7-(4-pyrrolidinobut-2-yn)oxy-4--methoxyisoflavone" with --7-(4-pyrrolidinobut-2-yn)oxy-4-methoxyisoflavone--.

Column 29, line 38, replace "3-(4-morpholinobut-2-yn)oxyxanthofle" with --3-(4-morpholinobut-2-yn)oxyxanthone--.

Column 30, line 46 insert the word --represents-- between "$R^4$" and "hydrogen".

Column 30, line 58 insert the word --represents-- between "$R^5$" and "hydrogen".

Column 32, line 13 insert the word --represents-- between "$R^5$" and "hydrogen".

UNITED STATES PATENT AND TRADEMARK OFFICE
CERTIFICATE OF CORRECTION

| | |
|---|---|
| PATENT NO. | : 6,608,089 B2 |
| APPLICATION NO. | : 10/075628 |
| DATED | : August 19, 2003 |
| INVENTOR(S) | : Ezio Bombardelli and Piero Valenti |

It is certified that error appears in the above-identified patent and that said Letters Patent is hereby corrected as shown below:

Column 33, line 35 replace "($R^{8), OR10}$" with --($R^8$), $OR^{10}$--.

Column 33, line 37 insert the word --is-- between "$R^{10}$" and "as".

Signed and Sealed this

Twenty-second Day of January, 2008

JON W. DUDAS
*Director of the United States Patent and Trademark Office*